(12) United States Patent
Blanquart

(10) Patent No.: US 12,200,364 B2
(45) Date of Patent: * Jan. 14, 2025

(54) CAMERA SCOPE ELECTRONIC VARIABLE PRISM

(71) Applicant: Medos International Sarl, Le Locle (CH)

(72) Inventor: Laurent Blanquart, Westlake Village, CA (US)

(73) Assignee: Medos International Sarl, Le Locle (CH)

( * ) Notice: Subject to any disclaimer, the term of this patent is extended or adjusted under 35 U.S.C. 154(b) by 0 days.

This patent is subject to a terminal disclaimer.

(21) Appl. No.: 17/549,745

(22) Filed: Dec. 13, 2021

(65) Prior Publication Data

US 2022/0103756 A1 Mar. 31, 2022

Related U.S. Application Data

(63) Continuation of application No. 16/445,111, filed on Jun. 18, 2019, now Pat. No. 11,202,014.

(60) Provisional application No. 62/694,893, filed on Jul. 6, 2018.

(51) Int. Cl.
*H04N 23/695* (2023.01)
*A61B 1/00* (2006.01)
*A61B 1/05* (2006.01)
*H04N 23/62* (2023.01)
*H04N 23/50* (2023.01)

(52) U.S. Cl.
CPC ....... *H04N 23/695* (2023.01); *A61B 1/00183* (2013.01); *A61B 1/05* (2013.01); *H04N 23/62* (2023.01); *H04N 23/555* (2023.01)

(58) Field of Classification Search
CPC .... H04N 23/695; H04N 23/62; H04N 23/555; H04N 23/54; H04N 23/50; H04N 23/55; H04N 23/69; A61B 1/00183; A61B 1/05; A61B 1/00096; A61B 1/045; G02B 23/24
See application file for complete search history.

(56) References Cited

U.S. PATENT DOCUMENTS

| | | |
|---|---|---|
| 3,818,902 A | 6/1974 | Kinoshita et al. |
| 3,939,840 A | 2/1976 | Storz |
| D271,698 S | 12/1983 | Shishido |
| 4,452,546 A | 6/1984 | Hiltebrandt et al. |
| 4,478,212 A | 10/1984 | Asano |
| 4,522,196 A | 6/1985 | Cunningham et al. |
| 4,600,940 A | 7/1986 | Sluyter |

(Continued)

FOREIGN PATENT DOCUMENTS

| | | |
|---|---|---|
| CN | 204410773 U | 6/2015 |
| CN | 110691178 A | 1/2020 |

(Continued)

*Primary Examiner* — Tat C Chio
(74) *Attorney, Agent, or Firm* — TechLaw Ventures, PLLC; Terrence J. Edwards

(57) ABSTRACT

A system, apparatus and methods for providing a scope having an imaging sensor which provides a two thousand pixel by two thousand pixel array of pixels. The imaging sensor allows for an angle of view to be changed within a field of view by selecting a one thousand pixel by one thousand pixel set within the two thousand pixel by two thousand pixel array of pixels containing imaging data that corresponds to a desired angle of view.

20 Claims, 18 Drawing Sheets

(56) References Cited

U.S. PATENT DOCUMENTS

| | | | |
|---|---|---|---|
| 4,611,888 A | 9/1986 | Prenovitz et al. |
| D288,936 S | 3/1987 | Feinbloom et al. |
| 4,722,000 A | 1/1988 | Chatenever |
| 4,820,043 A | 4/1989 | Diener |
| 4,844,071 A | 7/1989 | Chen et al. |
| 4,863,304 A | 9/1989 | Bauer et al. |
| 4,882,619 A | 11/1989 | Hasegawa et al. |
| RE34,002 E | 7/1992 | Adair |
| 5,156,141 A | 10/1992 | Krebs et al. |
| 5,313,306 A | 5/1994 | Kuban et al. |
| 5,329,887 A | 7/1994 | Ailinger et al. |
| 5,379,755 A | 1/1995 | Heckele |
| 5,456,673 A | 10/1995 | Ziegler et al. |
| 5,498,230 A | 3/1996 | Adair |
| 5,573,492 A | 11/1996 | Dianna et al. |
| 5,575,754 A | 11/1996 | Konomura |
| 5,643,176 A | 7/1997 | Persidsky |
| 5,682,199 A | 10/1997 | Lankford |
| 5,691,765 A | 11/1997 | Schieltz et al. |
| 5,707,340 A | 1/1998 | Hipp et al. |
| 5,772,678 A | 6/1998 | Thomason et al. |
| 5,800,341 A | 9/1998 | McKenna et al. |
| 5,807,237 A | 9/1998 | Tindel |
| 5,807,338 A | 9/1998 | Smith et al. |
| 5,810,770 A | 9/1998 | Chin et al. |
| 5,836,867 A | 11/1998 | Speier et al. |
| 5,868,773 A | 2/1999 | Danks et al. |
| 5,870,135 A | 2/1999 | Glatt et al. |
| 5,881,321 A | 3/1999 | Kivolowitz |
| 5,899,851 A | 5/1999 | Koninckx |
| 6,097,423 A | 8/2000 | Mattsson-Boze et al. |
| 6,100,972 A | 8/2000 | Harley et al. |
| 6,110,105 A | 8/2000 | Durell |
| 6,126,359 A | 10/2000 | Dittrich et al. |
| 6,196,967 B1 | 3/2001 | Lim et al. |
| 6,299,220 B1 | 10/2001 | Dittrich et al. |
| 6,328,691 B1 | 12/2001 | Rudischhauser |
| 6,339,446 B1 | 1/2002 | Miyoshi |
| 6,345,129 B1 | 2/2002 | Aharon |
| 6,364,830 B1 | 4/2002 | Durell |
| 6,371,909 B1 | 4/2002 | Hoeg et al. |
| 6,398,724 B1 | 6/2002 | May et al. |
| 6,450,992 B1 | 9/2002 | Cassidy |
| 6,471,637 B1 | 10/2002 | Green et al. |
| 6,478,731 B2 | 11/2002 | Speier et al. |
| 6,482,148 B1 | 11/2002 | Luke |
| 6,494,826 B1 | 12/2002 | Chatenever et al. |
| 6,537,210 B1 | 3/2003 | Wulfsberg |
| 6,540,668 B1 | 4/2003 | Schulz et al. |
| 6,560,013 B1 | 5/2003 | Ramsbottom |
| 6,626,828 B2 | 9/2003 | Dohi et al. |
| 6,632,173 B1 | 10/2003 | Kehr et al. |
| 6,638,216 B1 | 10/2003 | Durell |
| 6,648,817 B2 | 11/2003 | Schara et al. |
| 6,659,940 B2 | 12/2003 | Adler |
| 6,695,772 B1 | 2/2004 | Bon et al. |
| 6,695,774 B2 | 2/2004 | Hale et al. |
| 6,817,976 B2 | 11/2004 | Rovegno |
| 6,832,985 B2 | 12/2004 | Irion et al. |
| 6,855,106 B2 | 2/2005 | May et al. |
| 6,875,169 B2 | 4/2005 | Berci et al. |
| 6,947,074 B2 | 9/2005 | Koseki et al. |
| 7,037,258 B2 | 5/2006 | Chatenever et al. |
| 7,052,455 B2 | 5/2006 | Hale et al. |
| 7,134,992 B2 | 11/2006 | Schara et al. |
| 7,175,593 B2 | 2/2007 | Durell |
| 7,211,042 B2 | 5/2007 | Chatenever et al. |
| 7,221,522 B2 | 5/2007 | Tesar et al. |
| 7,237,990 B2 | 7/2007 | Deng |
| 7,241,262 B2 | 7/2007 | Adler et al. |
| 7,344,494 B2 | 3/2008 | Hoeg et al. |
| 7,374,533 B2 | 5/2008 | Hoeg et al. |
| 7,381,183 B2 | 6/2008 | Hale et al. |
| 7,387,605 B2 | 6/2008 | Frith |
| 7,427,262 B2 | 9/2008 | Bonningue et al. |
| 7,427,263 B2 | 9/2008 | Hoeg et al. |
| 7,517,314 B2 | 4/2009 | Hoeg et al. |
| 7,559,892 B2 | 7/2009 | Adler et al. |
| 7,578,786 B2 | 8/2009 | Boulais et al. |
| 7,585,273 B2 | 9/2009 | Adler et al. |
| 7,699,864 B2 | 4/2010 | Kick et al. |
| 7,783,133 B2 | 8/2010 | Dunki-Jacobs et al. |
| 7,833,152 B2 | 11/2010 | Chatenever et al. |
| 7,857,784 B2 | 12/2010 | Schmidberger et al. |
| 7,871,218 B2 | 1/2011 | Frey et al. |
| 7,909,756 B2 | 3/2011 | Hoeg et al. |
| 7,931,588 B2 | 4/2011 | Sarvazyan et al. |
| 7,956,887 B2 | 6/2011 | Hoeg et al. |
| 8,033,991 B2 | 10/2011 | Sarvazyan et al. |
| 8,072,483 B2 | 12/2011 | Tomioka |
| 8,157,726 B2 | 4/2012 | Melder |
| 8,186,350 B2 | 5/2012 | Matlock |
| 8,194,122 B2 | 6/2012 | Amling et al. |
| 8,202,290 B2 | 6/2012 | Smith |
| 8,203,644 B2 | 6/2012 | Shabtay et al. |
| 8,211,008 B2 | 7/2012 | Henzler |
| 8,377,089 B2 | 2/2013 | Lipchitz et al. |
| 8,485,968 B2 | 7/2013 | Weimer et al. |
| 8,500,173 B2 | 8/2013 | Zahler et al. |
| 8,500,769 B2 | 8/2013 | Deng |
| 8,547,423 B2 | 10/2013 | Ning |
| 8,758,234 B2 | 6/2014 | Hale et al. |
| 8,771,177 B2 * | 7/2014 | Hale ................. A61B 1/00179 |
| | | 600/176 |
| 8,814,782 B2 | 8/2014 | Hale et al. |
| 8,817,086 B2 | 8/2014 | Hoeg et al. |
| 8,834,358 B2 | 9/2014 | Mckinley et al. |
| 8,844,978 B2 | 9/2014 | Zahler et al. |
| 8,852,087 B2 | 10/2014 | Meyer et al. |
| 8,854,738 B2 | 10/2014 | Faber et al. |
| 8,870,758 B2 | 10/2014 | Dahmen et al. |
| 8,992,423 B2 | 3/2015 | Hale et al. |
| 9,033,871 B2 | 5/2015 | Schara et al. |
| 9,131,832 B2 | 9/2015 | Fouts et al. |
| 9,164,270 B2 | 10/2015 | Eisenkolb et al. |
| 9,182,577 B2 | 11/2015 | Hoeg et al. |
| 9,198,559 B2 | 12/2015 | Kesten et al. |
| 9,247,956 B2 | 2/2016 | Kleyman |
| 9,392,214 B2 | 7/2016 | Hanovich et al. |
| 9,392,930 B2 | 7/2016 | Lei et al. |
| 9,398,840 B2 | 7/2016 | Rehe |
| 11,032,481 B2 | 6/2021 | Blanquart |
| 11,202,014 B2 * | 12/2021 | Blanquart ............ H04N 23/695 |
| 2002/0103420 A1 | 8/2002 | Coleman et al. |
| 2006/0215013 A1 | 9/2006 | Jongsma et al. |
| 2006/0252995 A1 | 11/2006 | Hoeg et al. |
| 2008/0108870 A1 | 5/2008 | Wiita et al. |
| 2008/0234547 A1 | 9/2008 | Irion et al. |
| 2010/0004512 A1 | 1/2010 | Sueoka |
| 2010/0022838 A1 | 1/2010 | Hoeg |
| 2010/0030031 A1 | 2/2010 | Goldfarb et al. |
| 2010/0324372 A1 | 12/2010 | Buerk et al. |
| 2010/0324373 A1 | 12/2010 | Lei et al. |
| 2011/0046447 A1 | 2/2011 | Hoeg et al. |
| 2011/0196200 A1 | 8/2011 | Glozman et al. |
| 2011/0257485 A1 | 10/2011 | Baumann |
| 2012/0035420 A1 | 2/2012 | Weiger et al. |
| 2012/0035422 A1 | 2/2012 | Lei et al. |
| 2012/0078048 A1 | 3/2012 | Pauli et al. |
| 2012/0078049 A1 | 3/2012 | Pauli et al. |
| 2012/0136213 A1 | 5/2012 | Weimer et al. |
| 2012/0184820 A1 | 7/2012 | Dahmen et al. |
| 2013/0085338 A1 | 4/2013 | Buerk |
| 2014/0005478 A1 | 1/2014 | Kennedy, II et al. |
| 2014/0012078 A1 | 1/2014 | Coussa |
| 2014/0121459 A1 | 5/2014 | Hoeg et al. |
| 2014/0163319 A1 * | 6/2014 | Blanquart ............ A61B 1/0655 |
| | | 600/109 |
| 2014/0357947 A1 | 12/2014 | Fujitani |
| 2014/0375784 A1 | 12/2014 | Massetti |
| 2015/0045619 A1 | 2/2015 | Kumar et al. |
| 2015/0065799 A1 | 3/2015 | Hale et al. |
| 2015/0105620 A1 | 4/2015 | Oginski et al. |
| 2015/0313679 A1 | 11/2015 | Fukushima et al. |

(56) References Cited

U.S. PATENT DOCUMENTS

| | | |
|---|---|---|
| 2015/0374207 A1 | 12/2015 | Fukuoka |
| 2016/0066771 A1 | 3/2016 | Okamoto |
| 2016/0089181 A1* | 3/2016 | Johnson ............ A61B 1/00087 600/104 |
| 2016/0192831 A1 | 7/2016 | Schouwink et al. |
| 2016/0220099 A1 | 8/2016 | Schouwink et al. |
| 2016/0286160 A1 | 9/2016 | Hanovich et al. |
| 2017/0086933 A1 | 3/2017 | Ogawa et al. |
| 2018/0028052 A1 | 2/2018 | Kojo |
| 2018/0059293 A1 | 3/2018 | Sawai |
| 2018/0183983 A1 | 6/2018 | Taguchi |
| 2018/0196251 A1* | 7/2018 | Duckett, III ........... G02B 23/04 |
| 2018/0210188 A1 | 7/2018 | Ganapati et al. |
| 2019/0298321 A1* | 10/2019 | Intintoli ............ A61B 1/00094 |
| 2019/0307313 A1* | 10/2019 | Wade .................. A61B 90/361 |
| 2020/0014853 A1 | 1/2020 | Blanquart |
| 2020/0014855 A1 | 1/2020 | Blanquart |
| 2020/0374466 A1 | 11/2020 | Blanquart et al. |

FOREIGN PATENT DOCUMENTS

| | | |
|---|---|---|
| CN | 110691179 A | 1/2020 |
| DE | 10204718 A1 | 10/2002 |
| DE | 102007014739 A1 | 9/2008 |
| DE | 102009025659 A1 | 12/2010 |
| DE | 102009025660 A1 | 12/2010 |
| DE | 102009049143 A1 | 12/2010 |
| DE | 102010033423 A1 | 2/2012 |
| DE | 102010033425 A1 | 2/2012 |
| DE | 102010033427 A1 | 2/2012 |
| DE | 102010047884 A1 | 4/2012 |
| DE | 102014202612 A1 | 8/2015 |
| DE | 102014203316 A1 | 8/2015 |
| EP | 1844696 A1 | 10/2007 |
| EP | 1972259 A2 | 9/2008 |
| EP | 2147631 A1 | 1/2010 |
| EP | 2263518 A1 | 12/2010 |
| EP | 2263519 A2 | 12/2010 |
| EP | 3590409 A1 | 1/2020 |
| EP | 3590410 A1 | 1/2020 |
| JP | 2014021293 A | 2/2014 |
| WO | 2011044878 A1 | 4/2011 |

* cited by examiner

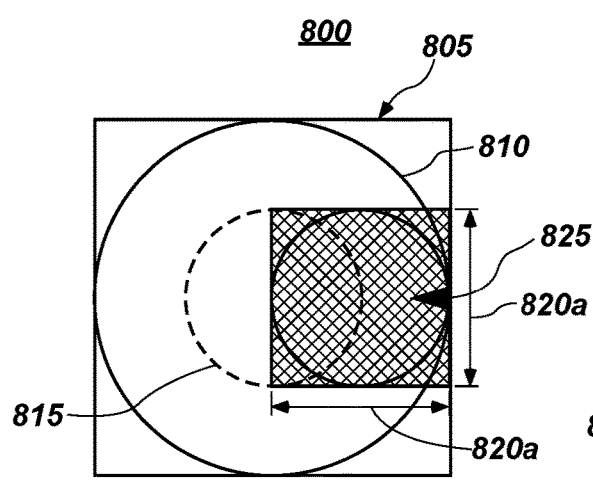
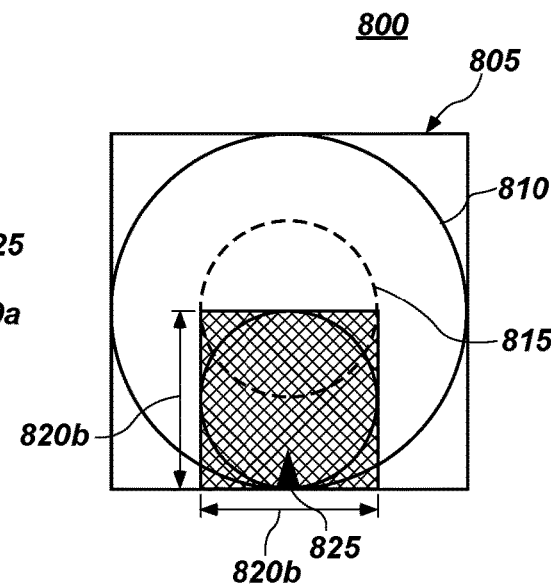
FIG. 8A        FIG. 8B
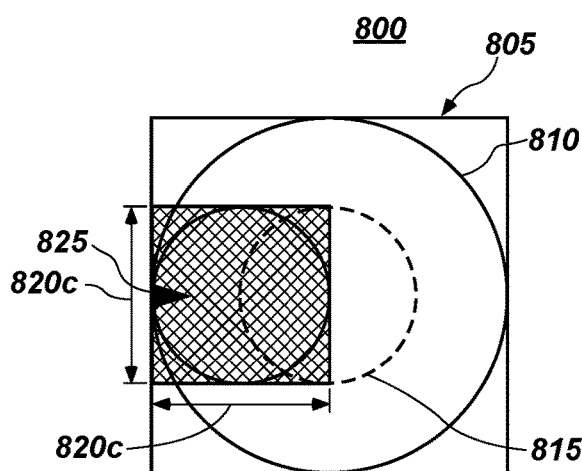
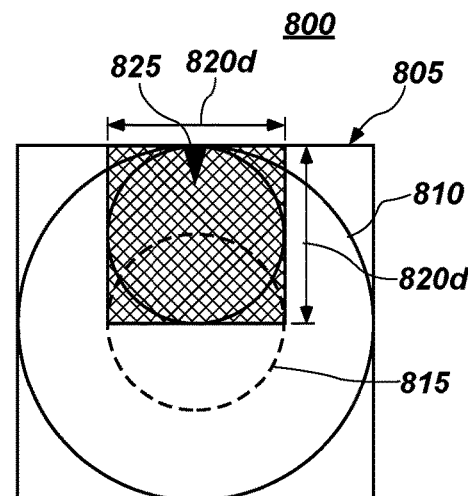
FIG. 8C        FIG. 8D

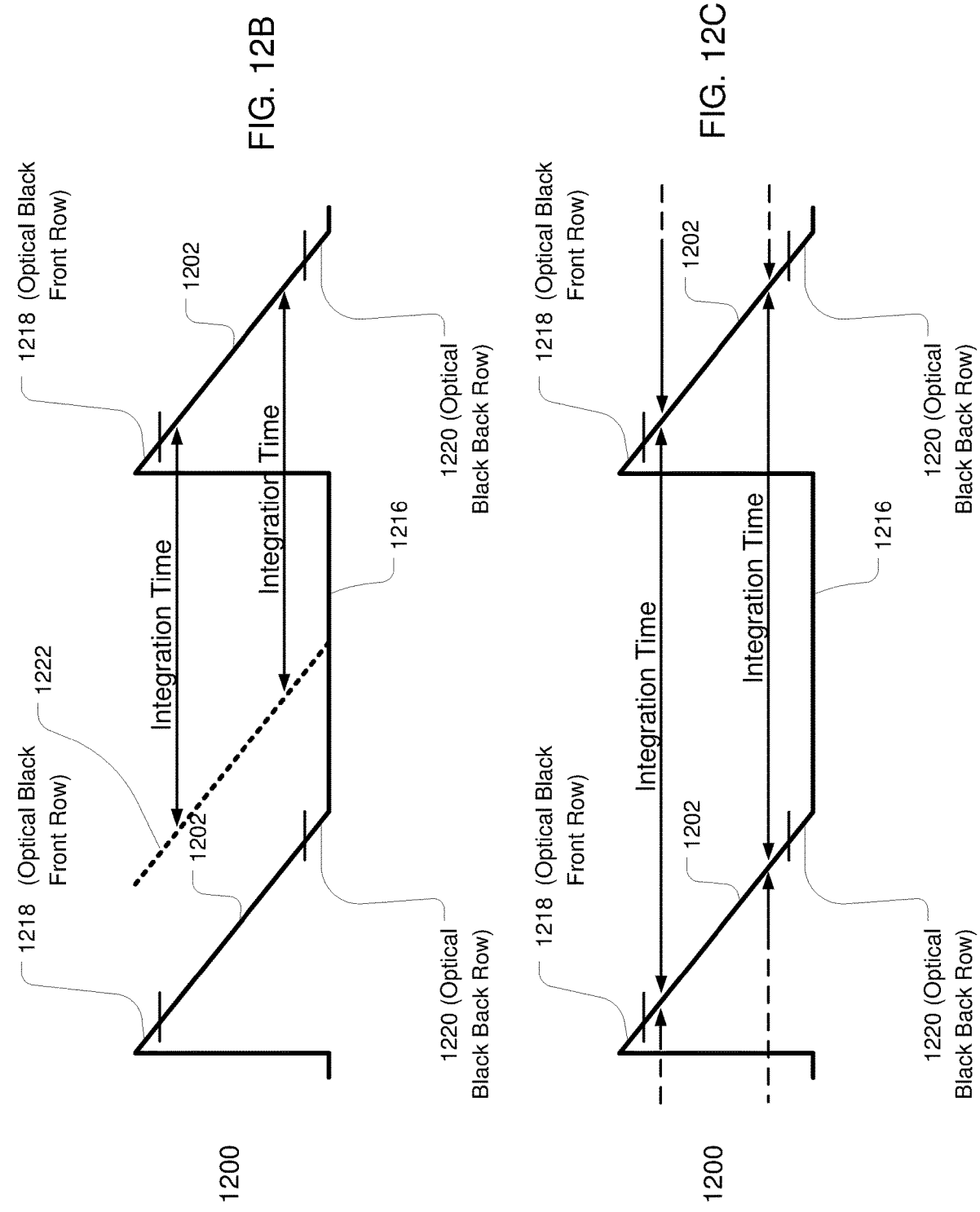

CAMERA SCOPE ELECTRONIC VARIABLE PRISM

CROSS-REFERENCE TO RELATED APPLICATIONS

This application is a continuation of U.S. patent application Ser. No. 16/445,111, filed Jun. 18, 2019 (now U.S. Pat. No. 11,202,014), which claims the benefit of U.S. Provisional Patent Application No. 62/694,893, filed Jul. 6, 2018, which are incorporated herein by reference in their entirety, including but not limited to those portions that specifically appear hereinafter, the incorporation by reference being made with the following exception: In the event that any portion of the above-referenced applications are inconsistent with this application, this application supercedes said portion of said above-referenced applications.

STATEMENT REGARDING FEDERALLY SPONSORED RESEARCH OR DEVELOPMENT

Not Applicable.

TECHNICAL FIELD

This disclosure relates generally to scopes of all types used to assist a surgeon during surgical procedures.

BACKGROUND

Endoscopic surgery is experiencing rapid growth in the medical field. Endoscopy is a minimally invasive surgical procedure that is used to analyze the interior of a body cavity or interior surfaces of an organ by inserting a tubular member into the body cavity through a minor or minimal incision. A conventional endoscope is generally an instrument with a light source and an image sensor or device for visualizing the interior a body cavity. A wide range of applications have been developed for the general field of endoscopes including, but not necessarily limited to: arthroscope, angioscope, bronchoscope, choledochoscope, colonoscope, cytoscope, duodenoscope, enteroscope, esophago-gastro-duodenoscope (gastroscope), laparoscope, laryngoscope, nasopharyngo-neproscope, sigmoidoscope, thoracoscope, and utererscope (hereinafter referred to generally as "endoscope" or "scope"). The advantages of endoscopy include smaller surgical incisions and less soft tissue damage. As a result, there is significantly less discomfort and pain for the patient as well as a decrease in recovery time.

The advantages of minimally invasive surgery performed with the help of an endoscope are well known and understood in the medical field. As a result, there have been a growing number of devices for use with endoscopes for delivering, for example, diagnostic, monitoring, treatment, operating instruments, tools, and accessories (collectively, "tools") into the observation field and working space of the physician's endoscope.

As part of forming an image of the surgical site, the endoscope includes a light source and an image sensor. Endoscopes may also incorporate more than one tubular member for observation or operation within the body, such as a working channel for passing diagnostic, monitoring, treatment, or surgical tools through the endoscope. Endoscopes include glass lenses and an adjustable ocular or eye piece, a lateral connection for a light conductor, an adaptor that allows focusing, and a camera head. This configuration is also called a video endoscope. Conventional endoscopes use physical prisms to direct light into a surgical scene. Unfortunately, the use of a physical prism also causes the tips of an endoscope to be angled and requires the user to rotate the physical prism to allow a surgeon to see different portions of a surgical scene.

Most scopes are implemented with a particular size aperture, such as, for example, a 5 mm scope. A 5 mm scope has no parts to be inserted into a body that exceed a 5 mm diameter. Conventional 5 mm scopes, or other scopes, are implemented with a zero degree (blunt) shaft tip or an angled shaft tip (e.g., between a range of about a thirty degree shaft tip to about a seventy degree shaft tip). In certain circumstances it is possible that other tips could be used to provide a narrower or wider field of view.

One drawback of this conventional technology is that in order to change a field of view from thirty degrees to seventy degrees, for example, a surgeon must withdraw a scope from a body of a person, remove the affixed thirty degree tip and apply a seventy degree tip to the scope (or use two scopes, one with a thirty degree tip and one with a seventy degree tip). Constant tip (or scope) changing is undesirable, however, because changing tips (or scopes) causes surgical delays that extend a length of a surgical procedure. Further, withdrawing and re-inserting a scope several times (or different scopes) risks that tissue will be damaged during the surgical procedure (e.g., accidentally hitting a nerve while reinserting a scope). Frequently, surgeons find that they would rather have a less ideal, or at least less desirable, view of a scene than constantly adjusting a field of view for different parts of a surgical procedure because of undesirability of adjusting or changing the tip of the scope to see a different field of view. Thus, when given the option between a less ideal view of a scene or switching or adjusting a scope, the surgeons will often operate with a less ideal view of a scene.

Accordingly, a need exists for surgeons to obtain their desired view of a scene when operating with a scope without withdrawing a scope from a body or without having to change physical devices or tips. A need further exists to provide true high definition view of a scene while having an ability to selectively select a desirable field of view.

The features and advantages of the disclosure will be set forth in the description that follows, and in part will be apparent from the description, or may be learned by the practice of the disclosure without undue experimentation. The features and advantages of the disclosure may be realized and obtained by means of the instruments and combinations particularly pointed out herein.

SUMMARY OF THE DISCLOSURE

In one embodiment, a system is disclosed. The system includes a scope, which further includes a lens. The system further includes a handpiece. The system also includes an imaging sensor. The imaging sensor includes a two thousand pixel by two thousand pixel array of pixels. The system further includes interface elements that, when actuated, cause an angle of view provided through the lens to be changed in a single image readout frame.

In another embodiment, a scope is disclosed. The scope includes a lens disposed in a distal tip of the scope. The scope includes a hand piece. The scope also includes an imaging sensor. The imaging sensor includes a two thousand pixel by two thousand pixel array of pixels. The scope further includes interface elements which, when actuated, cause an angle of view provided through the lens to be changed in a single readout frame.

In another embodiment, a method is disclosed. The method includes providing a scope having a lens in a distal tip of the scope. The scope further has one or more interface elements. A processor, for example, receives an indication from one of the one or more interface elements to change an angle of view provided to a display device. The processor identifies a sub-portion, for example one thousand pixel by one thousand pixel set of pixels on an image sensor having a two thousand pixel by two thousand pixel array of pixels that corresponds to the indicated angle of view. The processor receives imaging data from the one thousand pixel by one thousand pixel set of pixels corresponding to the indicated angle of view.

BRIEF DESCRIPTION OF THE DRAWINGS

The features and advantages of the disclosure will become apparent from a consideration of the subsequent detailed description presented in connection with the accompanying drawings in which:

FIGS. 8A-8D illustrate an embodiment of a view pattern implemented when the scope shown in FIG. 1 provides a 70° angle of view using a digital prism;

FIGS. 12A-12D illustrate operational cycles of a sensor used to construct one image frame;

DETAILED DESCRIPTION

Figure 1:
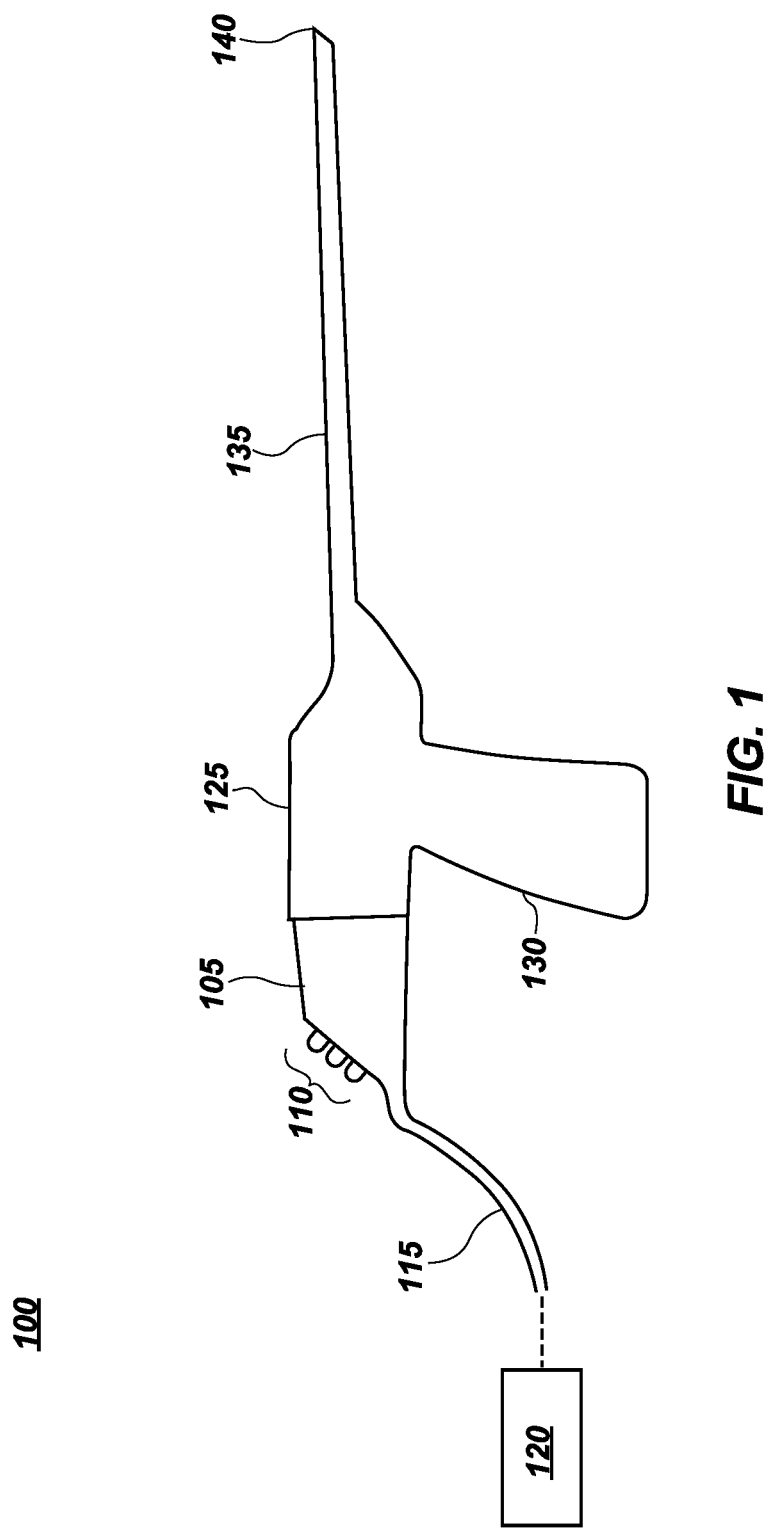
FIG. 1 illustrates an exemplary scope for use with an electronic variable prism.

For the purposes of promoting an understanding of the principles in accordance with the disclosure, reference will now be made to the embodiments illustrated in the drawings and specific language will be used to describe the same. It will nevertheless be understood that no limitation of the scope of the disclosure is thereby intended. Any alterations and further modifications of the inventive features illustrated herein, and any additional applications of the principles of the disclosure as illustrated herein, which would normally occur to one skilled in the relevant art and having possession of this disclosure, are to be considered within the scope of the disclosure claimed.

Before the devices, systems, methods and processes for providing single use imaging devices and an image or view optimizing assembly are disclosed and described, it is to be understood that this disclosure is not limited to the particular embodiments, configurations, or process steps disclosed herein as such embodiments, configurations, or process steps may vary somewhat. It is also to be understood that the terminology employed herein is used for the purpose of describing particular embodiments only and is not intended to be limiting since the scope of the disclosure will be limited only by the appended claims, if any, and equivalents thereof.

In describing and claiming the subject matter of the disclosure, the following terminology will be used in accordance with the definitions set out below.

It must be noted that, as used in this specification and the appended claims, the singular forms "a," "an," and "the" include plural referents unless the context clearly dictates otherwise.

It must be understood that "field of view" as used herein is intended to contemplate how much of an image can be seen in terms of degrees or angles as diffracted in liquids.

It must be understood that "angle of view" as used herein is intended to contemplate an angle at which a field of view is angled in degrees or angles as diffracted in liquids.

As used herein, the terms "comprising," "including," "containing," "characterized by," and grammatical equivalents thereof are inclusive or open-ended terms that do not exclude additional, unrecited elements or method steps.

As used herein, the phrase "consisting of" and grammatical equivalents thereof exclude any element, step, or ingredient not specified in the claim.

As used herein, the phrase "consisting essentially of" and grammatical equivalents thereof limit the scope of a claim to the specified materials or steps and those that do not materially affect the basic and novel characteristic or characteristics of the claimed disclosure.

As used herein, the term "active" as used in relation to a device or to electronic communication refers to any device or circuit, driven by hardware or software, that has decision making or logic processing capabilities regarding its operation and/or its condition. Conversely, the term "passive" as used in relation to an imaging device or to electronic communication refers to a hardware device that is written to and read from only, or a device that does not have any memory or other electronic, or physical tracking components and does not include any decision making or logic processing capabilities regarding its operation and/or its condition.

Referring now to the drawings, and specifically to FIG. 1, an embodiment of the features of the disclosure will be discussed generally. FIG. 1 illustrates a scope system 100 which provides a scope 125 for surgical use. Scope system 100 includes a hand piece 105 which connects to scope 125. Hand piece 105 may implement an image sensor, such as a CMOS sensor (not shown in FIG. 1 but discussed below). Hand piece 105 may further implement interactive elements 110, which may be implemented as buttons, dials, touch screens, or other conventional interactive elements known in the art. Handpiece 105 may be further connected to image acquisition and processing circuitry 120 by cable 115 which serves to communicate information from the CMOS sensor, pulses of light, and other information between image acquisition and processing circuitry 120 and hand piece 105. Image acquisition and processing circuitry 120 may include elements such as a light engine, a laser light engine, an image processor, a display unit for displaying images obtained from the CMOS image sensor, and other elements necessary to provide light pulses to a surgical scene at a distal tip of a scope and receive image information obtained by the CMOS sensor.

Scope 125 may include an optional handle 130 and various elements configured to transmit light to a distal end of scope 125 and obtain information from a surgical scene at a distal end of an endoscope. For example, various wires, transmission lines, fiber optic cables, lumens, and other elements may be disposed within scope 125 and may extend through a tube 135 to a distal end of scope 125.

At a distal end of tube 135, a prism (or a lens as will be discussed below) 140 may be disposed. For example, a prism 140 may be implemented to offset a field of view at a certain degree or angle. In one embodiment a 50° prism may be used to angle light being emitted from scope 125 into a surgical scene although any prism may be used to angle or diffract light such that light is directed at a particular angle between 0° and 90°. However, since most surgeons seem to prefer a view angle of 30° or 70°, a 50° prism is particularly suitable in this implementation because 30° and 70° are each 20° away from 50°. This particular implementation will be further discussed below. The image sensor, such as a CMOS sensor (not shown in FIG. 1 but discussed below), may be implemented within the distal end of the tube or scope 135.

Figure 2:
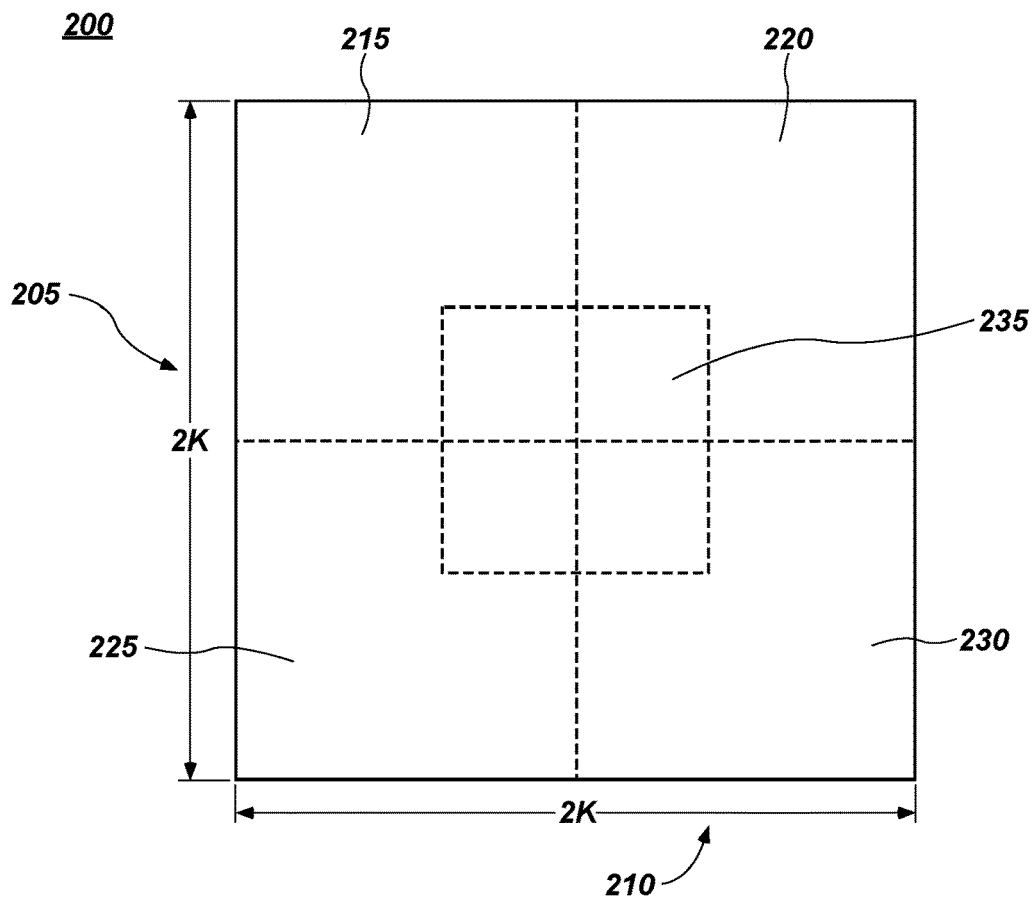
FIG. 2 illustrates a 4K image sensor which may be connected to the exemplary scope shown in FIG. 1.

FIG. 2 illustrates a 4K image sensor 200 which may be connected to the exemplary scope shown in FIG. 1. Image sensor 200 may be a CMOS sensor and may be referred to as a 4K sensor because image sensor 200 includes four million pixels arranged to have at least a height 205 of two thousand pixels and a width 210 of two thousand pixels. In other words, image sensor 200 may be a square sensor having a pixel array with four million individual pixels arranged to include a two thousand pixel by two thousand pixel square.

As shown in FIG. 2, image sensor 200 may be subdivided into smaller portions. That is to say, in an array of four million pixels, there exist a virtually limitless number of one thousand pixel by one thousand pixel sets in an array of pixels. A "set" of pixels and an "array" of pixels may be used interchangeably herein although a "set" of pixels in an array, for purposes of description, include a portion or fewer pixels than an available array of pixels. FIG. 2 illustrates a first pixel array 215 of one thousand pixels by one thousand pixels that occupies an upper left portion of a sensor and includes exactly one quarter of the total pixels in image sensor 200. FIG. 2 further illustrates a second pixel array 220, a third pixel array 225, and a fourth pixel array 230 which are each non-overlapping arrays occupying different portions of image sensor 200 and which are all one thousand pixels high by one thousand pixels wide. A fifth pixel array 235 is illustrated as occupying a center portion of image sensor 200 in that a left side of pixel array 235 is the same distance from a left edge of image sensor 200 as a right side of pixel array 235 is from a right edge of image sensor 200. Further, fifth pixel array 235 is identified such that a top side of pixel array 235 is the same distance from a top edge of image sensor 200 as a bottom side of pixel array 235 is from a bottom edge of image sensor 200.

First pixel array 215, second pixel array 220, third pixel array 225, fourth pixel array 230, and fifth pixel array 235 are merely instructive of five sub-pixel arrays that may be created from a two thousand by two thousand pixel array in image sensor 200. However, as previously discussed, a total number of unique one thousand pixel by one thousand pixel arrays may be virtually limitless. In other words, each individual pixel in image sensor 200 may be part of a unique one thousand pixel by one thousand pixel array that is different from every and any other array of one thousand pixels by one thousand pixels. Thus, the number of unique one thousand pixel by one thousand pixel arrays that may be selected from a two thousand by two thousand pixel array is quite large. Thus, a 4 k image sensor, such as image sensor 200, may be particularly suitable to provide a significant variety of one thousand by one thousand pixel arrays which may be selected to be used for a particular purpose, as will be discussed below.

Figure 3:
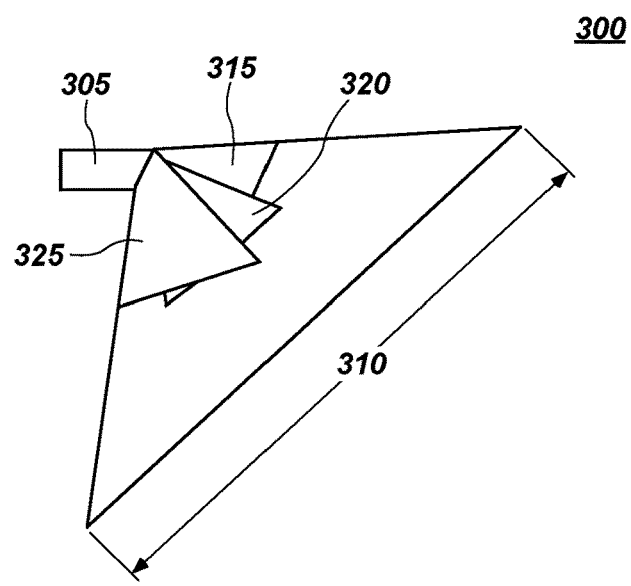
FIG. 3 illustrates an embodiment of a view pattern implemented when the scope shown in FIG. 1 incorporates a 50° prism.

FIG. 3 illustrates an embodiment of a view pattern 300 implemented when scope 125, which is shown and described with respect to FIG. 1 above, incorporates a 50° prism 305 which may be disposed in a distal end of scope 125. View pattern 300 from prism 305 may be projected onto a 4 k sensor, such as image sensor 200, discussed above with respect to FIG. 2 at a wide field of view 310. Field of view 310 may be wide enough to incorporate a 30° angle of view 315, a 50° angle of view 320, and a 70° angle of view 325, as shown in FIG. 3. Further, in an embodiment that uses a 50° prism, an 85° field of view may be obtained in liquids such as, for example, saline which is frequently the case in surgical situations. An 85° field of view also corresponds to a one thousand pixel by one thousand pixel array of pixels on a four million pixel array of pixels. Thus, information derived from each of 30° angle of view 315, 50° angle of view 320, and 70° angle of view 325 may be entirely captured by a 4 k image sensor, such as image sensor 200, discussed above. Specific implementations of view pattern 300 will be discussed below.

Figure 4A:
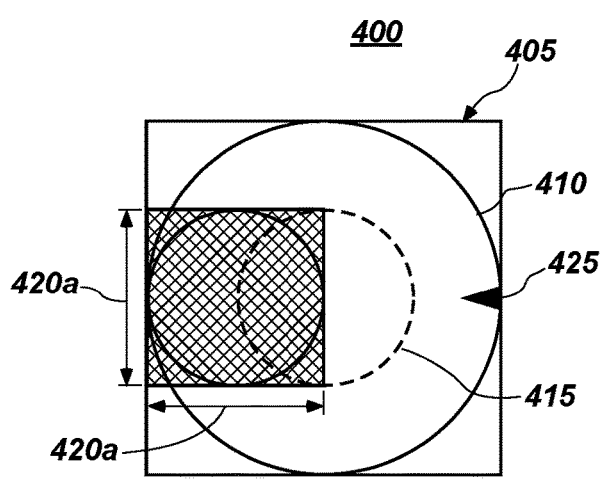
FIGS. 4A-4D illustrate an embodiment of a view pattern implemented when the scope shown in FIG. 1 incorporates a 50° prism and is adjusted to provide a 30° angle of view.

FIG. 4A illustrates an embodiment of a view pattern 400, which may be similar to view pattern 300 shown in FIG. 3, implemented when scope 125 shown in FIG. 1 incorporates a 50° prism and is adjusted to provide a 30° angle of view. View pattern 400 includes a representation of an image sensor 405 which may be a 4K image sensor. Image sensor 405 may be implemented in a manner similar in implementation and description to image sensor 200, discussed above. View pattern 400 includes a wide field of view 410 which encompasses a total field of view that may be viewed through a 50° prism. As shown in FIG. 4A, field of view 410 is laid on image sensor 405 to illustrate an approximate position for each pixel collecting image information from a scene on image sensor 405. View pattern 400 further illustrates a center focal point 415 which represents a center portion of image sensor 405.

View pattern 400 further includes a representation of a specific one thousand pixel by one thousand pixel array 420a that corresponds to a 30° of a scene at a particular portion of the view identified by notch 425. By manipulation of scope 125 using interface elements 110, shown in FIG. 1, a surgeon may change or rotate a particular 30° angle of view to view different 30° portions of a surgical scene. Notch 425 provides an orientation point to a surgeon for which 30° portion of a surgical scene the surgeon is looking at such that the surgeon may identify which direction is up, down, left, or right.

However, as the surgeon rotates an angle of view, the corresponding positions of pixels on pixel array 405 which are receiving the desired image information change. In other words, a particular one thousand pixel by one thousand pixel array 420a may be associated with a particular angle of view designated by notch 425. As shown in FIG. 4A, a 30° angle of view may cause image information to be stored in a one thousand pixel by one thousand pixel array 420a that is disposed on image sensor 405 directly opposite of notch 425. In this manner, a location of image data in image sensor 405 which is desired by a surgeon at a 30° view may be identified and displayed on a display for the surgeon using techniques further described below. Effectively, the focus point of the 50° prism is shifted by 20° to the left (based on the position of notch 425) in FIG. 4A to focus on a 30° field of view identified by the circular area within one thousand pixel by one thousand pixel array 420a.

Figure 4B:
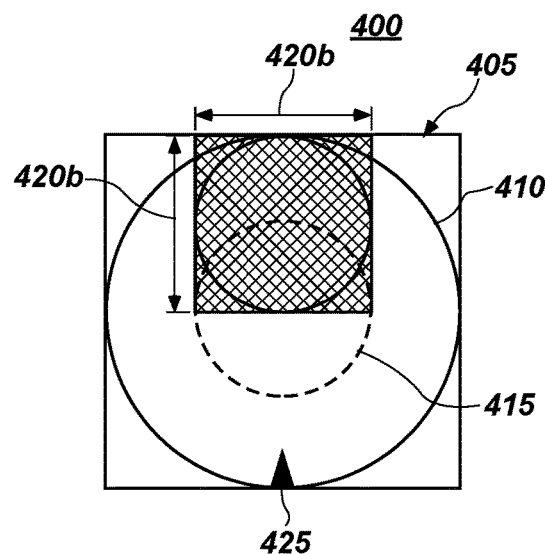
Figure 4C:
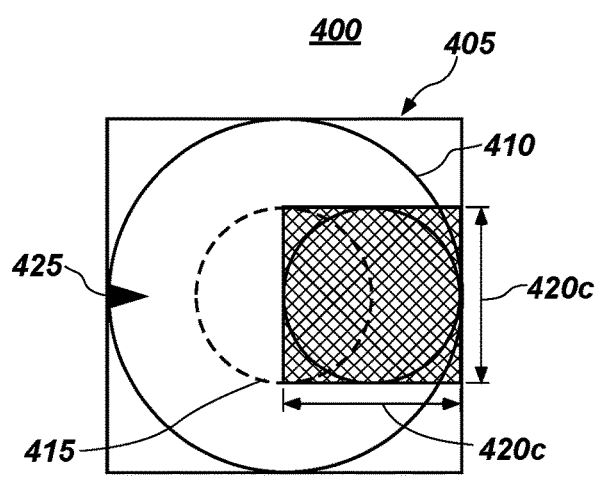
Figure 4D:
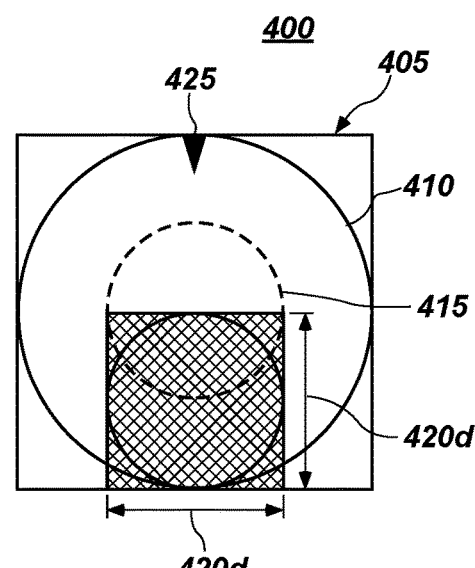

FIGS. 4B-4D illustrate view patterns 400 which are altered by a surgeon rotating notch 425 to view specific 30° portions of a field of view. FIG. 4B illustrates a view where a surgeon is looking at a top portion of a field of view. FIG. 4C illustrates a view where a surgeon is looking at a right portion of a field of view. FIG. 4D illustrates a view where a surgeon is looking at a bottom portion of a field of view.

One further advantage of this implementation is that a surgeon may still rotate an angle of view through a field of view as desired. However, a surgeon may also switch an angle of view from 30° to 50° or 70°, for example, implemented as one of interface elements 110. A further advantage is that one thousand pixel by one thousand pixel array 420a within image sensor 405 may be read at approximately 240 frames per second. Since desired image quality may be obtained with a vastly slower read out rate than 240 frames per second, image acquisition and processing circuitry 120 may identify minute rotations of notch 425 and recalculate a location of a new one thousand pixel by one thousand pixel array 420a as scope 100 is rotated. In other words, a new one thousand by one thousand pixel array 420a may be identified with each one of the 240 frames and still provide a desirable image output. This allows a surgeon to maintain a constant view while rotating notch 425.

Figure 5A:
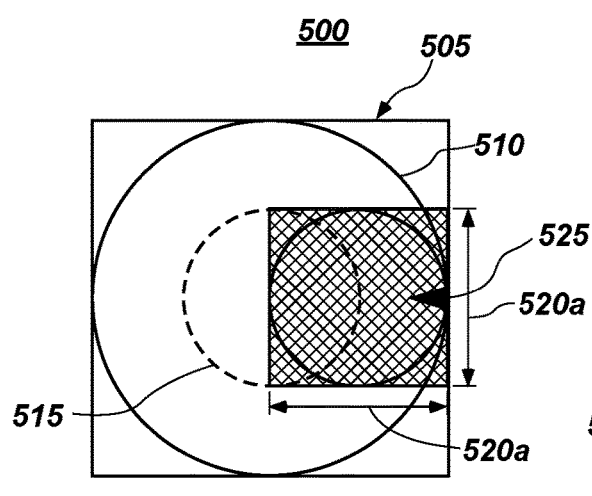
FIGS. 5A-5D illustrate an embodiment of a view pattern implemented when the scope shown in FIG. 1 incorporates a 50° prism and is adjusted to provide a 70° angle of view.

FIG. 5A illustrates an embodiment of a view pattern 500, which may be similar to view pattern 300 shown in FIG. 3, implemented when scope 125 shown in FIG. 1 incorporates a 50° prism and is adjusted to provide a 70° angle of view. View pattern 500 includes a representation of an image sensor 505 which may be a 4K image sensor. Image sensor 505 may be implemented in a manner similar in implementation and description to image sensor 200, discussed above. View pattern 500 includes a wide field of view 510 which encompasses a total field of view that may be viewed through a 50° prism. As shown in FIG. 5A, field of view 510 is laid on image sensor 505 to illustrate an approximate position for each pixel collecting image information from a scene on image sensor 505. View pattern 500 further illustrates a center focal point 515 which represents a center portion of image sensor 505.

View pattern 500 further includes a representation of a specific one thousand pixel by one thousand pixel array 520a that corresponds to a 70° of a scene at a particular portion of the view identified by notch 525. By manipulation of scope 125 using interface elements 110, shown in FIG. 1, a surgeon may change or rotate a particular 70° angle of view to view different 70° portions of a surgical scene. Notch 525 provides an orientation point to a surgeon for which 70° portion of a surgical scene the surgeon is looking at such that the surgeon may identify which direction is up, down, left, or right.

However, as the surgeon rotates an angle of view, the corresponding positions of pixels on pixel array 505 which are receiving the desired image information change. In other words, a particular one thousand pixel by one thousand pixel array 520a may be associated with a particular angle of view designated by notch 525. As shown in FIG. 5A, a 70° angle of view may cause image information to be stored in a one thousand pixel by one thousand pixel array 520a that is disposed on image sensor 505 directly on (e.g., bisected by) notch 525. In this manner, a location of image data in image sensor 505 which is desired by a surgeon at a 70° view may be identified and displayed on a display for the surgeon using techniques further described below. Effectively, the focus point of the 50° prism is shifted by 20° to the right (based on the position of notch 525) in FIG. 5A to focus on a 70° field of view identified by the circular area within one thousand pixel by one thousand pixel array 520a.

Figure 5B:
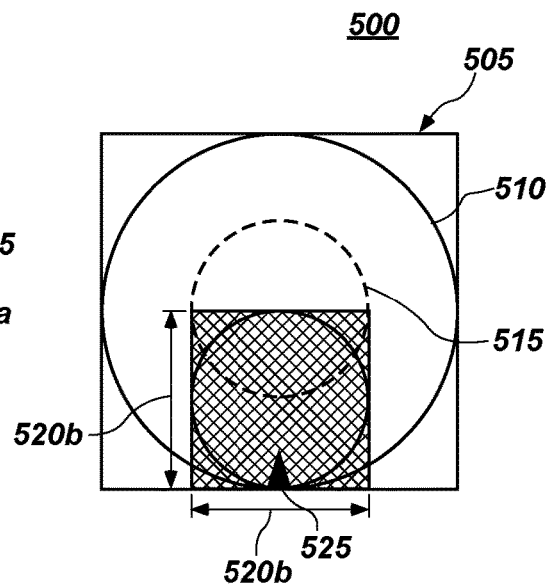
Figure 5C:
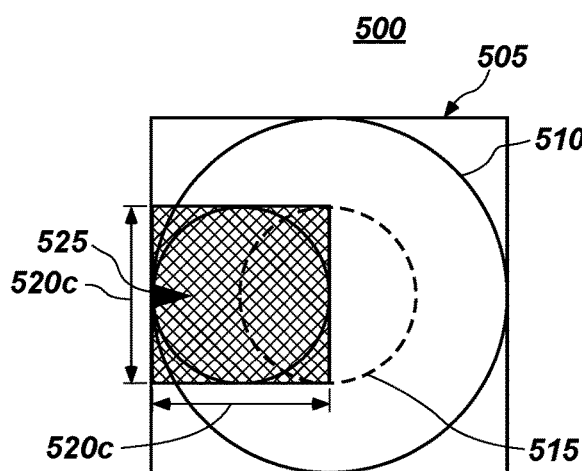
Figure 5D:
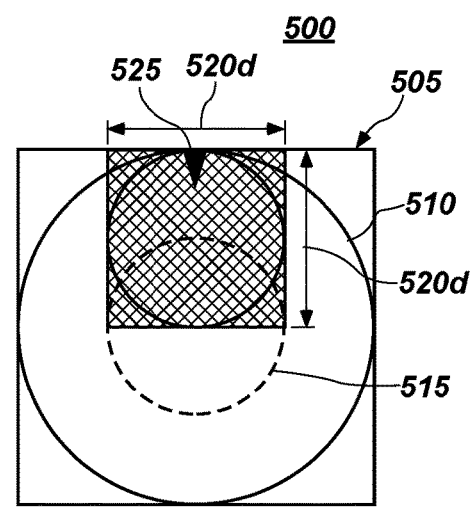

FIGS. 5B-5D illustrate view patterns 500 which are altered by a surgeon rotating notch 525 to view specific 70° portions of a field of view. FIG. 5B illustrates a view where a surgeon is looking at a top portion of a field of view. FIG. 5C illustrates a view where a surgeon is looking at a right portion of a field of view. FIG. 5D illustrates a view where a surgeon is looking at a bottom portion of a field of view.

One further advantage of this implementation is that a surgeon may still rotate an angle of view through a field of view as desired. However, a surgeon may also switch an angle of view from 70° to 50° or 30° with nothing more than a press of a button, for example, implemented as one of interface elements 110. A further advantage is that one thousand pixel by one thousand pixel array 520a within image sensor 505 may be read at approximately 240 frames per second. Since desired image quality may be obtained with a vastly slower read out rate than 240 frames per second, image acquisition and processing circuitry 120 may identify minute rotations of notch 525 and recalculate a location of a new one thousand pixel by one thousand pixel array 520a as scope 100 is rotated. In other words, a new one thousand by one thousand pixel array 520a may be identified with each one of the 240 frames and still provide a desirable image output. This allows a surgeon to maintain a constant view while rotating notch 525.

Figure 6A:
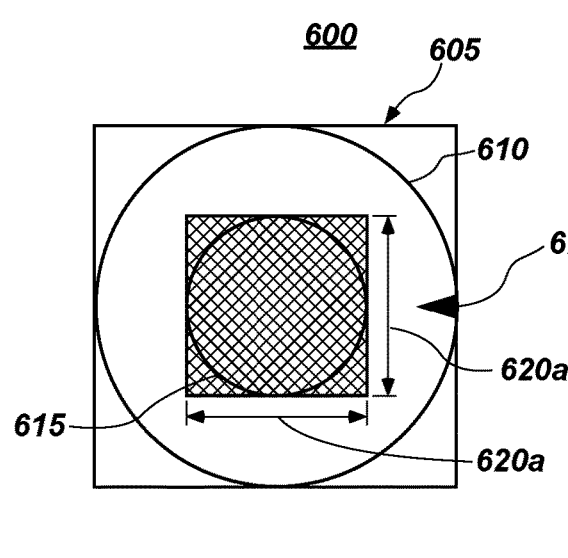
FIGS. 6A-6D illustrate an embodiment of a view pattern implemented when the scope shown in FIG. 1 incorporates a 50° prism and is adjusted to provide a 50° angle of view.

FIG. 6A illustrates an embodiment of a view pattern 600, which may be similar to view pattern 300 shown in FIG. 3, implemented when scope 125 shown in FIG. 1 incorporates a 50° prism and is adjusted to provide a 50° angle of view. View pattern 600 includes a representation of an image sensor 605 which may be a 4K image sensor. Image sensor 605 may be implemented in a manner similar in implementation and description to image sensor 200, discussed above. View pattern 600 includes a wide field of view 610 which encompasses a total field of view that may be viewed through a 50° prism. As shown in FIG. 6A, field of view 610 is laid on image sensor 605 to illustrate an approximate position for each pixel collecting image information from a scene on image sensor 605. View pattern 600 further illustrates a center focal point 615 which represents a center portion of image sensor 605.

View pattern 600 further includes a representation of a specific one thousand pixel by one thousand pixel array 620a that corresponds to a 50° view of a scene at a particular portion of the view identified by notch 625. By manipulation of scope 125 using interface elements 110, shown in FIG. 1, a surgeon may change or rotate a particular 50° angle of view to view different 50° portions of a surgical scene. Notch 625 provides an orientation point to a surgeon for which 50° portion of a surgical scene the surgeon is looking at such that the surgeon may identify which direction is up, down, left, or right.

In this unique embodiment, as the surgeon rotates an angle of view, the corresponding positions of pixels on image sensor 605 which are receiving the desired image information remain in the same place on image sensor 605 because a 50° prism is installed on scope 125. Thus, a 50° angle of view may always be associated with one particular thousand pixel by one thousand pixel array 620a regardless of the position of notch 625. While notch 625 may direct scope to identify different 50° angles of view (e.g., 50° looking up or 50° looking down), the location of pixels receiving image data remains the same by use of a 50° prism. Accordingly, as shown in FIG. 6A, a 50° angle of view may cause image information to be stored in a one thousand pixel by one thousand pixel array 620a that is disposed such that a center pixel of the one thousand pixel by one thousand pixel array 620 is a center pixel of the two thousand by two thousand pixel array that makes up image sensor 605. In this manner, a location of image data in image sensor 605 which is desired by a surgeon at a 50° view may be identified and displayed on a display for the surgeon using techniques further described below.

Figure 6B:
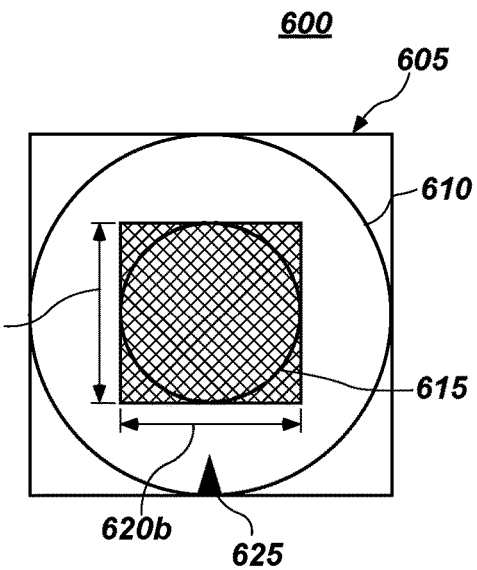
Figure 6C:
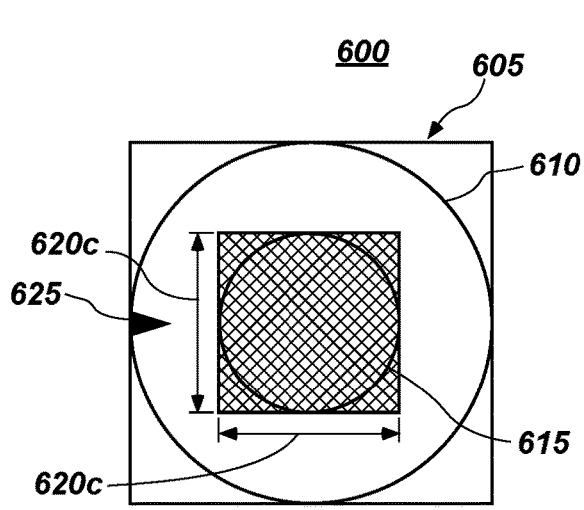
Figure 6D:
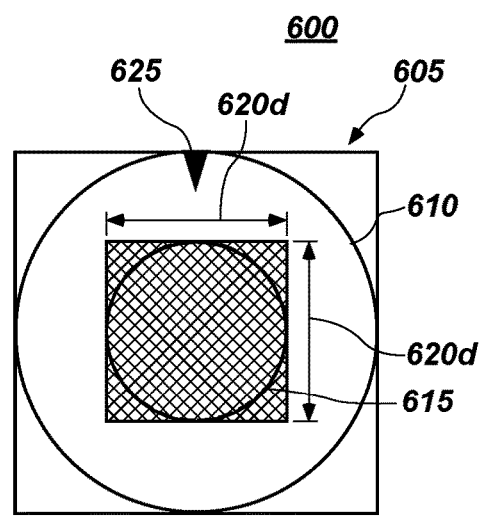

FIGS. 6B-6D illustrate view patterns 600 which are altered by a surgeon rotating notch 625 to view specific 50° portions of a field of view. FIG. 6B illustrates a view where a surgeon is looking at a top portion of a field of view. FIG. 6C illustrates a view where a surgeon is looking at a right portion of a field of view. FIG. 6D illustrates a view where a surgeon is looking at a bottom portion of a field of view.

One further advantage of this implementation is that a surgeon may still rotate an angle of view through a field of view as desired. However, a surgeon may also switch an angle of view from 50° to 30° or 70° with nothing more than a press of a button, for example, implemented as one of interface elements 110. A further advantage is that one thousand pixel by one thousand pixel array 620a within image sensor 605 may be read at approximately 240 frames per second. Since desired image quality may be obtained with a vastly slower read out rate than 240 frames per second, image acquisition and processing circuitry 120 may identify minute rotations of notch 625 and read the known location of the one thousand pixel by one thousand pixel array 620a associated with a 50° angle of view as scope 100 is rotated. In other words, a the one thousand by one thousand pixel array 620a may be read with each one of the 240 frames and provide a desirable image output. This allows a surgeon to maintain a constant view while rotating notch 625.

Figure 7A:
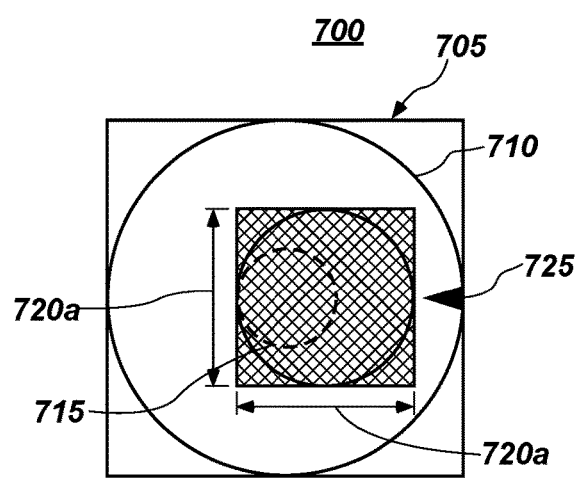
FIGS. 7A-7D illustrate an embodiment of a view pattern implemented when the scope shown in FIG. 1 provides a 30° angle of view using a digital prism.

FIG. 7A illustrates an embodiment of a view pattern 700, which corresponds to an implementation of scope 125 shown in FIG. 1 which does not, as before, incorporate a 50° prism. Rather, in the embodiment of FIG. 7A, scope 125 is fitted with a wide field of view lens, such as a 180° lens with a 0° offset. Other lenses may be substituted for a 180° lens. Typically, any lens between 125° and 180° is suitable in this implementation. Lenses used in this embodiment may or may not be fisheye lenses. However, it is to be noted that this embodiment does not use a prism to bend an angle of view and there is a 0° offset in this embodiment. However, by identifying certain portions of an image sensor, such as image sensor 705, a particular angle of view within the field of view of the lens may be provided in a manner that is consistent with a surgeon's expectations and experience with a scope, using the techniques discussed below.

View pattern 700 includes a representation of an image sensor 705 which may be a 4K image sensor. Image sensor 705 may be implemented in a manner similar in implementation and description to image sensor 200, discussed above. View pattern 700 includes a wide field of view 710 which encompasses a total field of view that may be viewed through a wide field of view lens. As shown in FIG. 7A, field of view 710 is laid on image sensor 705 to illustrate an approximate position for each pixel collecting image information from a scene on image sensor 705. View pattern 700 further illustrates a center focal point 715 which represents a center portion of image sensor 705.

View pattern 700 further includes a representation of a specific one thousand pixel by one thousand pixel array 720a that corresponds to a 30° of a scene at a particular portion of the view identified by notch 725. In this embodiment, however, no physical rotation of scope 125 is necessary. Rather, a surgeon interfacing with interface elements 110 may digitally alter both the angle of view and field of view. In response, image acquisition and processing circuitry 120 may identify a one thousand pixel by one thousand pixel array 720a to produce a desired view which, in FIG. 7A is a 30° angle of view looking to the right. Image sensor 705 effectively captures every 30° angle of view and can selectively produce a corresponding image by reading out portions of image sensor 705 that contain data corresponding to a desired 30° angle of view. Notch 725 may still be provided on a display to provide a surgeon with a reference point in the surgical scene such that the surgeon may identify which direction is up, down, left, or right.

However, as the surgeon digitally rotates an angle of view by use of interface elements 110 on scope 125, the corresponding positions of pixels on pixel array 705 which are receiving the desired image information change. In other words, a particular one thousand pixel by one thousand pixel array 720a may be associated with a particular angle of view designated by notch 725. As shown in FIG. 7A, a 30° angle of view may cause image information to be stored in a one thousand pixel by one thousand pixel array 720a that is disposed on image sensor 705 may include a center portion of image sensor 705 be centered vertically about the center point of image sensor 705 and extend one thousand pixels in a direction towards notch 725. In this manner, a location of image data in image sensor 705 which is desired by a surgeon at a 30° angle of view may be identified and displayed on a display for the surgeon using techniques further described below. Effectively, the focus point of a lens may be digitally shifted by 30° to provide a selected 30° angle of view in a field of view defined by the lens.

Figure 7B:
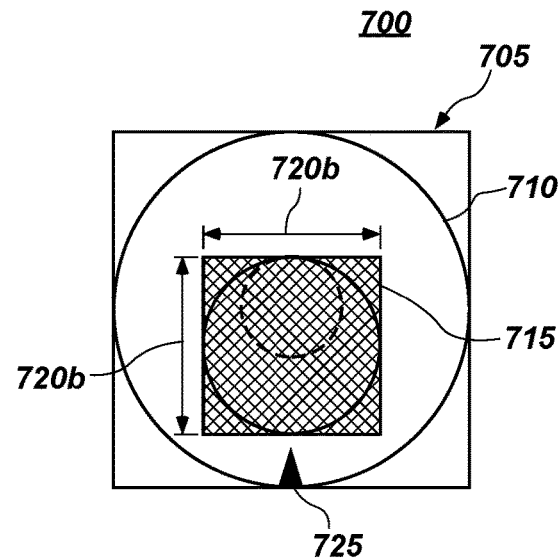
Figure 7C:
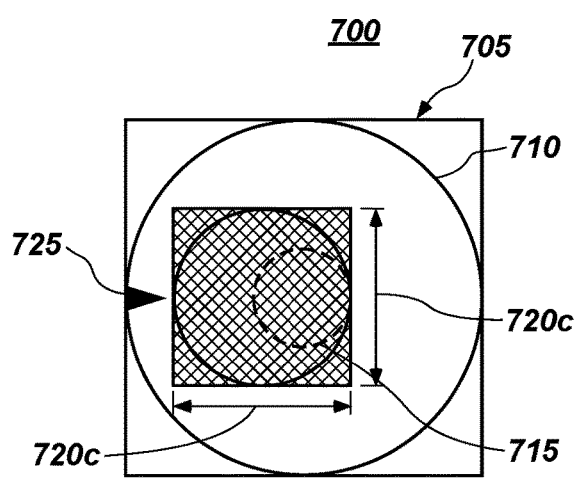
Figure 7D:
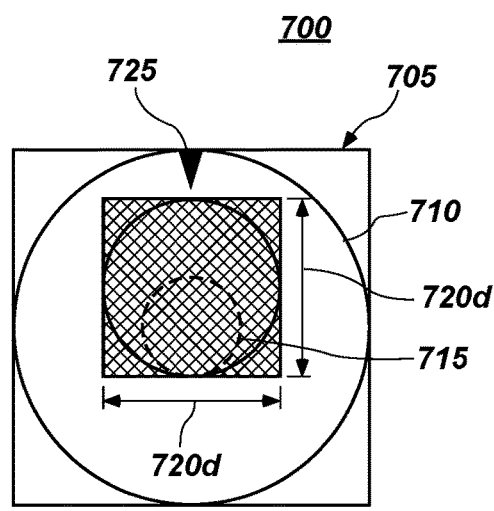

FIGS. 7B-7D illustrate view patterns 700 which are altered by a surgeon digitally rotating notch 725 to view specific 30° portions of a field of view. FIG. 7B illustrates a view where a surgeon is looking at a top portion of a field of view. FIG. 7C illustrates a view where a surgeon is looking at a right portion of a field of view. FIG. 7D illustrates a view where a surgeon is looking at a bottom portion of a field of view.

One further advantage of this implementation is that a surgeon may digitally rotate an angle of view through a field of view as desired while also digitally switching an angle of view from 70° to 0° or 30°, for example, using one or more of interface elements 110. A further advantage is that one thousand pixel by one thousand pixel array 720a within image sensor 705 may be read at approximately 240 frames per second. Since desired image quality may be obtained with a vastly slower read out rate than 240 frames per second, image acquisition and processing circuitry 120 may react to minute digital rotations of notch 725 and recalculate a location of a new one thousand pixel by one thousand pixel array 720a as scope 100 is digitally rotated. In other words, a new one thousand by one thousand pixel array 720a may be identified with each one of the 240 frames and still provide a desirable image output. This allows a surgeon to maintain a constant view while digitally rotating notch 725.

FIG. 8A illustrates an embodiment of a view pattern 800, which corresponds to an implementation of scope 125 shown in FIG. 1 which does not, as before, incorporate a prism. Rather, in the embodiment of FIG. 8A, scope 125 is fitted with a wide field of view lens, such as a 180° lens with a 0° offset. Other lenses may be substituted for a 180° lens. Typically, any lens between 125° and 180° is suitable in this implementation. Lenses used in this embodiment may or may not be fisheye lenses. However, it is to be noted that this embodiment does not use a prism to bend an angle of view and there is a 0° offset in this embodiment. However, by identifying certain portions of an image sensor, such as image sensor 805, a particular angle of view within the field of view of the lens may be provided in a manner that is consistent with a surgeon's expectations and experience with a scope, using the techniques discussed below.

View pattern 800 includes a representation of an image sensor 805 which may be a 4K image sensor. Image sensor 805 may be implemented in a manner similar in implementation and description to image sensor 200, discussed above. View pattern 800 includes a wide field of view 810 which encompasses a total field of view that may be viewed through a wide field of view lens. As shown in FIG. 8A, field of view 810 is laid on image sensor 805 to illustrate an approximate position for each pixel collecting image information from a scene on image sensor 805. View pattern 800 further illustrates a center focal point 815 which represents a center portion of image sensor 805.

View pattern 800 further includes a representation of a specific one thousand pixel by one thousand pixel array 820a that corresponds to a 70° of a scene at a particular portion of the view identified by notch 825. In this embodiment, however, no physical rotation of scope 125 is necessary. Rather, a surgeon interfacing with interface elements 110 may digitally alter both the angle of view and field of view. In response, image acquisition and processing circuitry 120 may identify a one thousand pixel by one thousand pixel array 820a to produce a desired view which, in FIG. 7A is a 70° angle of view looking to the right. Image sensor 805 effectively captures every 70° angle of view and can selectively produce a corresponding image by reading out portions of image sensor 805 that contain data corresponding to a desired 70° angle of view. Notch 825 may still be provided on a display to provide a surgeon with a reference point in the surgical scene such that the surgeon may identify which direction is up, down, left, or right.

However, as the surgeon digitally rotates an angle of view by use of interface elements 110 on scope 125, the corresponding positions of pixels on pixel array 705 which are receiving the desired image information change. In other words, a particular one thousand pixel by one thousand pixel array 820a may be associated with a particular angle of view designated by notch 825. As shown in FIG. 8A, a 70° angle of view may cause image information to be stored in a one thousand pixel by one thousand pixel array 820a that is disposed on image sensor 805 may include a center pixel of image sensor 705 being disposed in a center of a vertical edge of the one thousand pixel by one thousand pixel array and extending one thousand pixels from that vertical edge in a direction towards notch 725. In this manner, a location of image data in image sensor 805 which is desired by a surgeon at a 70° angle of view may be identified and displayed on a display for the surgeon using techniques further described below. Effectively, the focus point of a lens may be digitally shifted by 70° to provide a selected 70° angle of view in a field of view defined by the lens.

FIGS. 8B-8D illustrate view patterns 800 which are altered by a surgeon digitally rotating notch 825 to view specific 70° portions of a field of view. FIG. 8B illustrates a view where a surgeon is looking at a top portion of a field of view (the one thousand pixel by one thousand pixel array being defined by a center point of image sensor 805 disposed in a center of a horizontal edge of the one thousand pixel by one thousand pixel array). FIG. 8C illustrates a view where a surgeon is looking at a right portion of a field of view. FIG. 8D illustrates a view where a surgeon is looking at a bottom portion of a field of view.

One further advantage of this implementation is that a surgeon may digitally rotate an angle of view through a field of view as desired while also digitally switching an angle of view from 70° to 0° or 30°, for example, using one or more of interface elements 110. A further advantage is that one thousand pixel by one thousand pixel array 820a within image sensor 805 may be read at approximately 240 frames per second. Since desired image quality may be obtained with a vastly slower read out rate than 240 frames per second, image acquisition and processing circuitry 120 may react to minute digital rotations of notch 825 and recalculate a location of a new one thousand pixel by one thousand pixel array 820a as scope 100 is digitally rotated. In other words, a new one thousand by one thousand pixel array 820a may be identified with each one of the 240 frames and still provide a desirable image output. This allows a surgeon to maintain a constant view while digitally rotating notch 825.

Figure 9A:
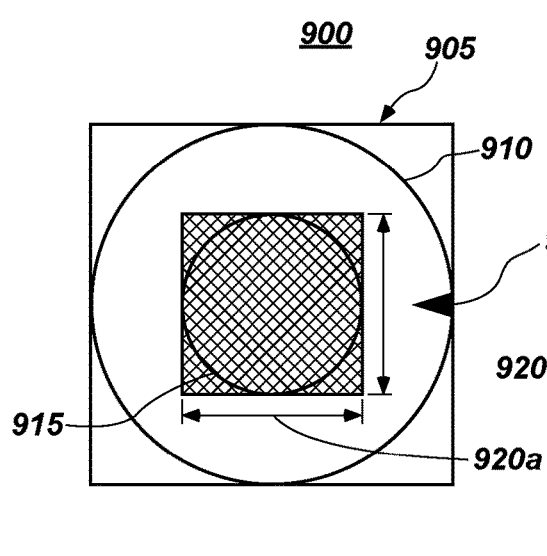
FIGS. 9A-9D illustrate an embodiment of a view pattern implemented when the scope shown in FIG. 1 provides a 50° angle of view using a digital prism.

FIG. 9A illustrates an embodiment of a view pattern 900, which corresponds to an implementation of scope 125 shown in FIG. 1 which does not, as before, incorporate a prism. Rather, in the embodiment of FIG. 8A, scope 125 is fitted with a wide field of view lens, such as a 180° lens with a 0° offset. Other lenses may be substituted for a 180° lens. Typically, any lens between 125° and 180° is suitable in this implementation. Lenses used in this embodiment may or may not be fisheye lenses. However, it is to be noted that this embodiment does not use a prism to bend an angle of view and there is a 0° offset in this embodiment. However, by identifying certain portions of an image sensor, such as image sensor 905, a particular angle of view within the field of view of the lens may be provided in a manner that is consistent with a surgeon's expectations and experience with a scope, using the techniques discussed below.

View pattern 900 includes a representation of an image sensor 905 which may be a 4K image sensor. Image sensor 905 may be implemented in a manner similar in implementation and description to image sensor 200, discussed above. View pattern 900 includes a wide field of view 910 which encompasses a total field of view that may be viewed through a lens. As shown in FIG. 9A, field of view pattern 910 is laid on image sensor 905 to illustrate an approximate position for each pixel collecting image information from a scene on image sensor 905. View pattern 900 further illustrates a center focal point 915 which represents a center portion of image sensor 905.

View pattern 900 further includes a representation of a specific one thousand pixel by one thousand pixel array 920a that corresponds to a 0° view of a scene at a particular portion of the view identified by notch 925. By manipulation of scope 125 using interface elements 110, shown in FIG. 1, a surgeon may digitally change or digitally rotate a particular 0° angle of view to view different 0° portions of a surgical scene. Notch 925 provides an orientation point to a surgeon for which 0° portion of a surgical scene the surgeon is looking at such that the surgeon may identify which direction is up, down, left, or right.

In this unique embodiment, as the surgeon digitally rotates an angle of view, the corresponding positions of pixels on image sensor 905 which are receiving the desired image information remain in the same place on image sensor 905 because a lens which does not bend an angle of light is installed on scope 125. Thus, a 0° angle of view may always be associated with one particular thousand pixel by one thousand pixel array 920a regardless of the position of notch 925. While notch 925 may direct scope to identify different 0° angles of view (e.g., 0° looking up or 0° looking down), the location of pixels receiving image data remains the same by use of a lens. Accordingly, as shown in FIG. 9A, a 0° angle of view may cause image information to be stored in a one thousand pixel by one thousand pixel array 920a that is disposed such that a center pixel of the one thousand pixel by one thousand pixel array 920 is a center pixel of the two thousand by two thousand pixel array that makes up image sensor 905. In this manner, a location of image data in image sensor 905 which is desired by a surgeon at a 0° view may be identified and displayed on a display for the surgeon using techniques further described below.

Figure 9B:
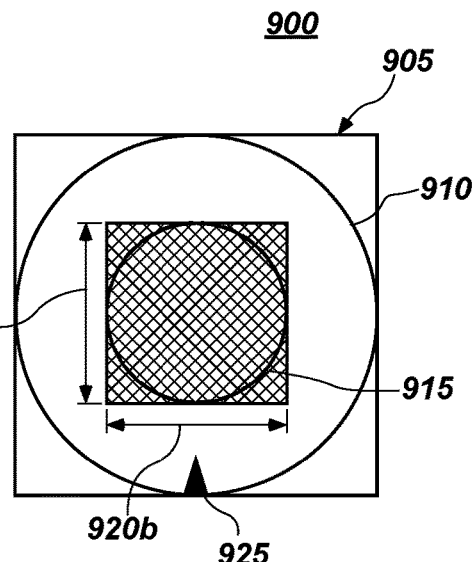
Figure 9C:
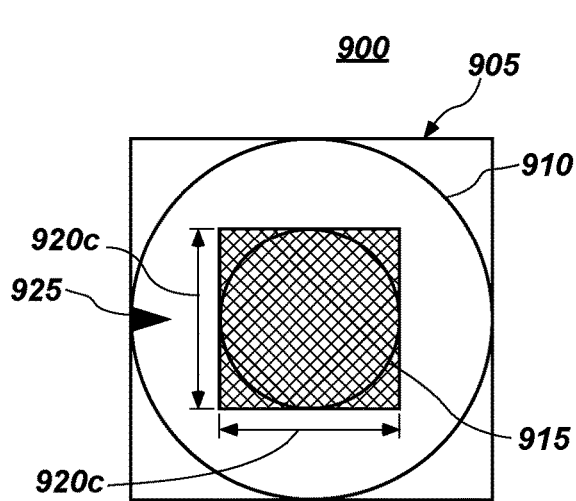
Figure 9D:
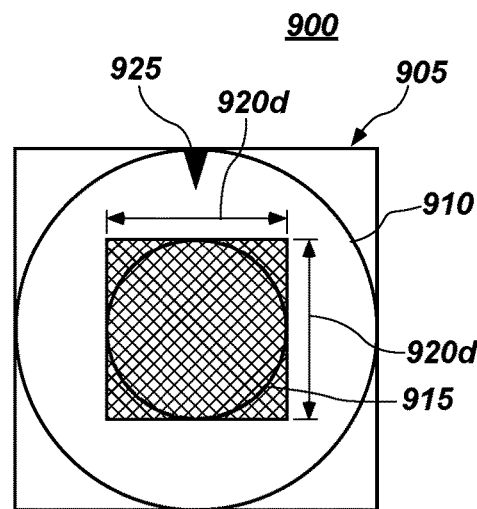

FIGS. 9B-9D illustrate view patterns 900 which are altered by a surgeon digitally rotating notch 925 to view specific 0° portions of a field of view. FIG. 9B illustrates a view where a surgeon is looking at a top portion of a field of view. FIG. 9C illustrates a view where a surgeon is looking at a right portion of a field of view. FIG. 9D illustrates a view where a surgeon is looking at a bottom portion of a field of view.

One further advantage of this implementation is that a surgeon may digitally rotate an angle of view through a field of view as desired while also digitally switching an angle of view from 0° to 30° or 70°, for example, using one or more of interface elements 110. A further advantage is that one thousand pixel by one thousand pixel array 920a within image sensor 905 may be read at approximately 240 frames per second. Since desired image quality may be obtained with a vastly slower read out rate than 240 frames per second, image acquisition and processing circuitry 120 may react to minute digital rotations of notch 925. The one thousand by one thousand pixel array 920a associated with a 0° may be read out with each one of the 240 frames and still provide a desirable image output. This allows a surgeon to maintain a constant view while digitally rotating notch 925.

Figure 10:
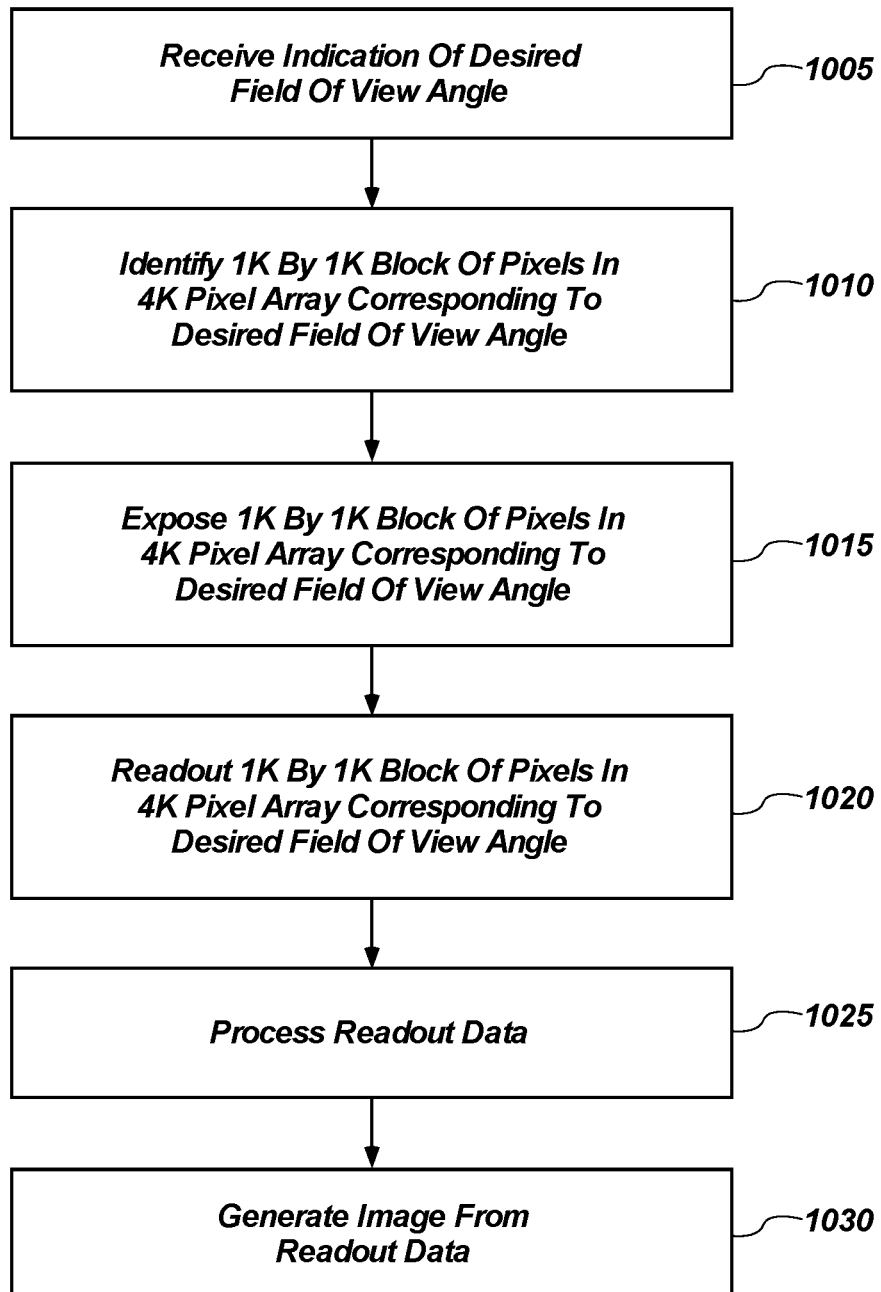
FIG. 10 illustrates a method for identifying a selection of pixels in an 4K array of pixels to provide a view at a particular angle of view.

FIG. 10 illustrates a method 1000 for identifying a selection of pixels in an 4K array of pixels to provide a view at a particular angle of view in a field of view. Method 1000 begins at step 1005 at which image acquisition and processing circuitry 120, shown in FIG. 1, may by use of a processor, which will be described in more detail below, receive an indication of a desired field of view angle for scope 125. For example, a surgeon may manipulate interface elements 110 to indicate that the surgeon desires a 0°, a 30°, a 50° or a 70° field of view angle, depending on embodiment. As part of step 1005 and receiving an identification of a desired field of view angle for scope 125, the processor may receive an indication of an angle of view by physical or digital manipulation of a notch, such as notch 425 described in FIGS. 4A-4D and other notches described in other figures. Once the processor has determined a desired field of view and angle of view for scope 125, the processor may, at step 1010 identify a one thousand pixel by one thousand pixel array of pixels in a 4 k pixel array on an image sensor which within which image information for the particular selected field of view and angle of view has been identified.

Once the particular one thousand pixel by one thousand pixel array associated with a particular selected field of view and angle of view has been identified, the identified one thousand pixel by one thousand pixel array may be exposed to receive image data from a surgical scene at step 1015. For example, light may be emitted into a surgical scene which may be sensed by the pixels in an image sensor, such as image sensor 200, shown in FIG. 2. These pixels in the image sensor store light information which may be used to provide a video display of the surgical scene. This light information received by exposure of the pixels on the image sensor may be read out of the one thousand pixel by one thousand pixel array at step 1020. At step 1025, the processor may process the relevant read out data and generate a video image from the readout data at step 1030. In this manner, the various frames captured at 240 frames per second may be assembled together to provide a video based view of a surgical scene at a field of view and angle of view determined by a surgeon.

Advantageously, since only one quarter of an image sensor, such as image sensor 200 shown in FIG. 2 is needed to provide a particular field of view and angle of view at a particular surgical scene, when using a 4 k image sensor, other pixels that may receive image information may be used for other purposes. For example, if a frame rate was slowed from 240 frames per second, these pixels may be used to receiving additional information such as infrared information, color information, spectroscopy information, ultraviolet information, augmented reality information, or other information from a surgical scene.

It may be further possible to eliminate a data line connection to the camera head for receiving information from interface elements 110 by encoding the information from the interface elements in a video stream such that an image sensor, such as image sensor 200 encodes a button status and transmits the information to the image acquisition and processing circuitry, such as image acquisition and processing circuitry 120 shown in FIG. 1. The image acquisition and processing circuitry may therefore respond appropriately to interaction with interface elements 110.

It is also possible that instead of reading just a one thousand pixel by one thousand pixel array, a processor may readout the entire 4K sensor albeit with a lower frame rate of 60 frames per second. However, using the foregoing techniques, it is possible to provide two angles of view for a particular field of view simultaneously by identifying pixels that overlap between two different angles of view, if any. In this manner a video stream for a first angle of view may be provided to a first display while a video stream for a second angle or view may be provided to a second display simultaneously. It is also possible that these different views may be overlaid on each other. For example, an augmented reality view may be captured by an image sensor while the desired angle of view is displayed such that the augmented reality view may be overlaid on the same display.

Figure 11:
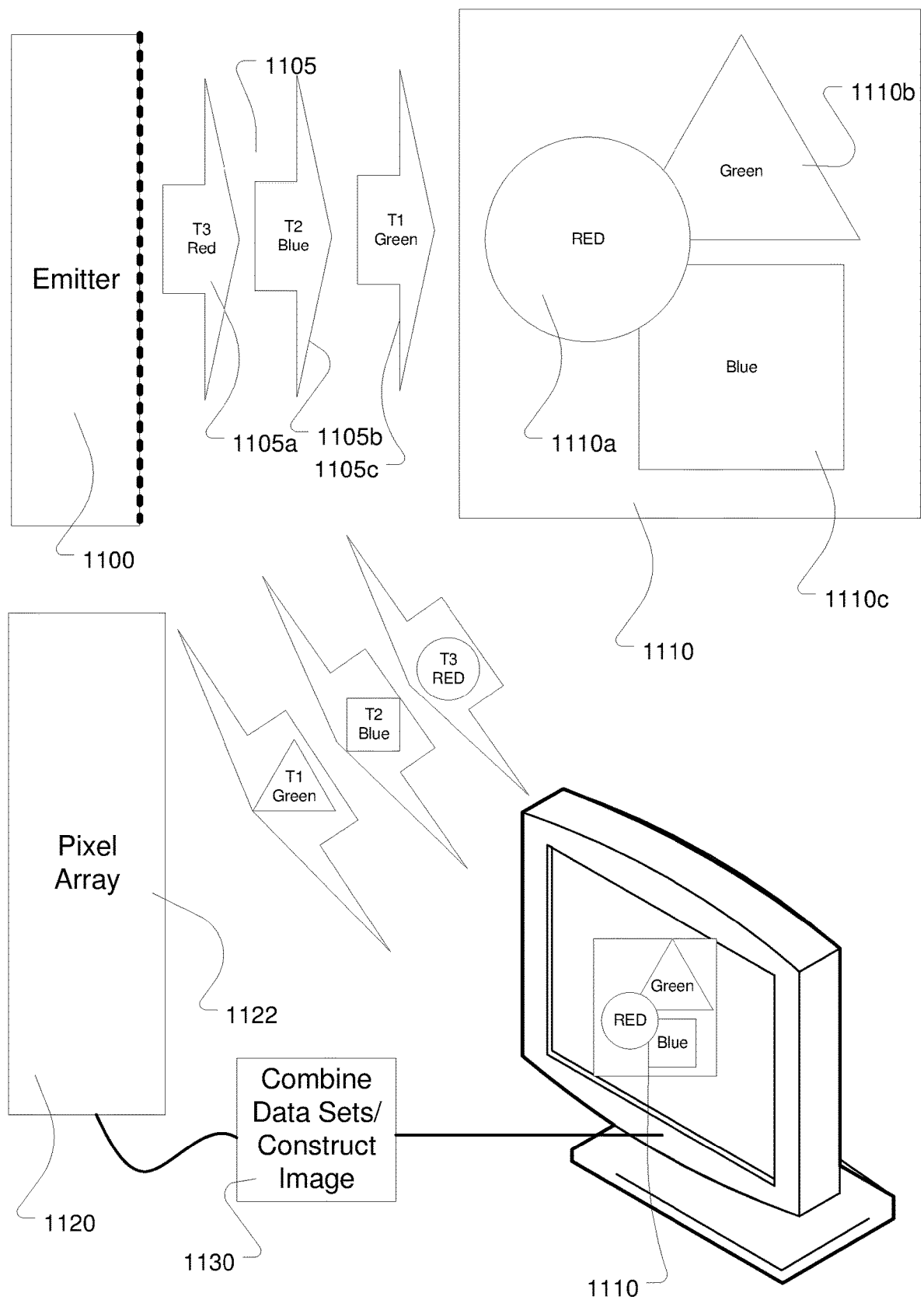
FIG. 11 illustrates a schematic view of an embodiment of a system of a 4K sensor and an electromagnetic emitter in operation for use in producing an image in a light deficient environment using the scope shown in FIG. 1.

FIG. 11 illustrates a schematic view of an embodiment of a system of a 4K sensor and an electromagnetic emitter in operation for use in producing an image in a light deficient environment using the scope shown in FIG. 1. FIG. 11 illustrates a schematic view of a paired sensor and an electromagnetic emitter in operation for use in producing an image in a light deficient environment. Such a configuration allows for increased functionality in light controlled or ambient light deficient environments.

It should be noted that as used herein the term "light" is both a particle and a wavelength and is intended to denote electromagnetic radiation that is detectable by a pixel array and may include wavelengths from the visible and non-visible spectrums of electromagnetic radiation. The term "partition" is used herein to mean a pre-determined range of wavelengths of the electromagnetic spectrum that is less than the entire spectrum, or in other words, wavelengths that make up some portion of the electromagnetic spectrum. As used herein, an emitter is a light source that may be controllable as to the portion of the electromagnetic spectrum that is emitted or that may operate as to the physics of its components, the intensity of the emissions, or the duration of the emission, or all of the above. An emitter may emit light in any dithered, diffused, or collimated emission and may be controlled digitally or through analog methods or systems. As used herein, an electromagnetic emitter is a source of a burst of electromagnetic energy and includes light sources, such as lasers, LEDs, incandescent light, or any light source that can be digitally controlled.

A pixel array of an image sensor may be paired with an emitter electronically, such that they are synced during operation for both receiving the emissions and for the adjustments made within the system. As can be seen in FIG. 11, an emitter 1100 may be tuned to emit electromagnetic radiation in the form of a laser, which may be pulsed in order to illuminate an object 1110. The emitter 1100 may pulse at an interval that corresponds to the operation and functionality of a pixel array 1122. The emitter 1100 may pulse light in a plurality of electromagnetic partitions 1105, such that the pixel array receives electromagnetic energy and produces a data set that corresponds (in time) with each specific electromagnetic partition 1105. For example, FIG. 11 illustrates a system having a monochromatic sensor 1120 having a pixel array (black and white) 1122 and supporting circuitry, which pixel array 1122 is sensitive to electromagnetic radiation of any wavelength. Pixel array 1122 may be a 4 k pixel array implemented as a 4 k image sensor similar to, for example, image sensor 200 shown in FIG. 2. The light emitter 1100 illustrated in the figure may be a laser emitter that is capable of emitting a red electromagnetic partition 1105a, a blue electromagnetic partition 1105b, and a green electromagnetic partition 1105c in any desired sequence. It will be appreciated that other light emitters 1100 may be used in FIG. 11 without departing from the scope of the disclosure, such as digital or analog based emitters.

During operation, the data created by the monochromatic sensor 1120 for any individual pulse may be assigned a specific color partition, wherein the assignment is based on the timing of the pulsed color partition from the emitter 1100. Even though the pixels 1122 are not color dedicated they can be assigned a color for any given data set based on a priori information about the emitter.

In one embodiment, three data sets representing RED, GREEN and BLUE electromagnetic pulses may be combined to form a single image frame. It will be appreciated that the disclosure is not limited to any particular color combination or any particular electromagnetic partition, and that any color combination or any electromagnetic partition may be used in place of RED, GREEN and BLUE, such as Cyan, Magenta and Yellow; Ultraviolet; infra-red; any combination of the foregoing, or any other color combination, including all visible and non-visible wavelengths, without departing from the scope of the disclosure. In the figure, the object 1110 to be imaged contains a red portion 1110a, green portion 1110b and a blue portion 1110c. As illustrated in the figure, the reflected light from the electromagnetic pulses only contains the data for the portion of the object having the specific color that corresponds to the pulsed color partition. Those separate color (or color interval) data sets can then be used to reconstruct the image by combining the data sets at 1130.

Figure 12:
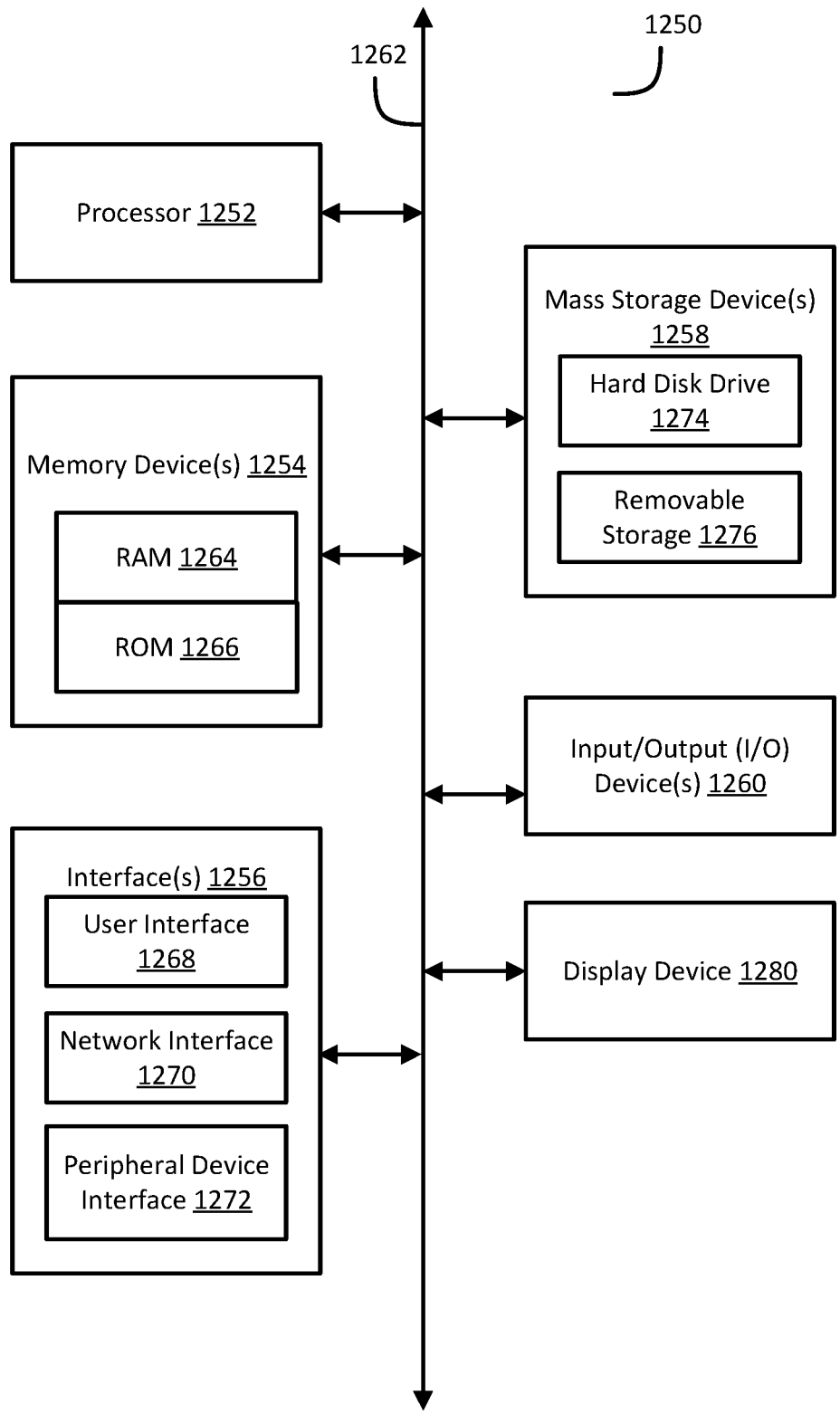
FIG. 12 illustrates a schematic view of complementary system hardware.

As illustrated in FIG. 12, implementations of the present disclosure may comprise or utilize a special purpose or general-purpose computer, including computer hardware, such as, for example, one or more processors and system memory, as discussed in greater detail below. Implementations within the scope of the present disclosure may also include physical and other computer-readable media for carrying or storing computer-executable instructions and/or data structures. Such computer-readable media can be any available media that can be accessed by a general purpose or special purpose computer system. Computer-readable media that store computer-executable instructions are computer storage media (devices). Computer-readable media that carry computer-executable instructions are transmission media. Thus, by way of example, and not limitation, implementations of the disclosure can comprise at least two distinctly different kinds of computer-readable media: computer storage media (devices) and transmission media.

Computer storage media (devices) includes RAM, ROM, EEPROM, CD-ROM, solid state drives ("SSDs") (e.g., based on RAM), Flash memory, phase-change memory ("PCM"), other types of memory, other optical disk storage, magnetic disk storage or other magnetic storage devices, or any other medium which can be used to store desired program code means in the form of computer-executable instructions or data structures and which can be accessed by a general purpose or special purpose computer.

A "network" is defined as one or more data links that enable the transport of electronic data between computer systems and/or modules and/or other electronic devices. In an implementation, a sensor and camera control unit may be networked in order to communicate with each other, and other components, connected over the network to which they are connected. When information is transferred or provided over a network or another communications connection (either hardwired, wireless, or a combination of hardwired or wireless) to a computer, the computer properly views the connection as a transmission medium. Transmissions media can include a network and/or data links, which can be used to carry desired program code means in the form of computer-executable instructions or data structures and which can be accessed by a general purpose or special purpose computer. Combinations of the above should also be included within the scope of computer-readable media.

Further, upon reaching various computer system components, program code means in the form of computer-executable instructions or data structures that can be transferred automatically from transmission media to computer storage media (devices) (or vice versa). For example, computer-executable instructions or data structures received over a network or data link can be buffered in RAM within a network interface module (e.g., a "NIC"), and then eventually transferred to computer system RAM and/or to less volatile computer storage media (devices) at a computer system. RAM can also include solid state drives (SSDs or PCIx based real time memory tiered storage, such as FusionIO). Thus, it should be understood that computer storage media (devices) can be included in computer system components that also (or even primarily) utilize transmission media.

Computer-executable instructions comprise, for example, instructions and data which, when executed at a processor, cause a general purpose computer, special purpose computer, or special purpose processing device to perform a certain function or group of functions. The computer executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

Those skilled in the art will appreciate that the disclosure may be practiced in network computing environments with many types of computer system configurations, including, personal computers, desktop computers, laptop computers, message processors, control units, camera control units, hand-held devices, hand pieces, multi-processor systems, microprocessor-based or programmable consumer electronics, network PCs, minicomputers, mainframe computers, mobile telephones, PDAs, tablets, pagers, routers, switches, various storage devices, and the like. It should be noted that any of the above mentioned computing devices may be provided by or located within a brick and mortar location. The disclosure may also be practiced in distributed system environments where local and remote computer systems, which are linked (either by hardwired data links, wireless data links, or by a combination of hardwired and wireless data links) through a network, both perform tasks. In a distributed system environment, program modules may be located in both local and remote memory storage devices.

Further, where appropriate, functions described herein can be performed in one or more of: hardware, software, firmware, digital components, or analog components. For example, one or more application specific integrated circuits (ASICs) or field programmable gate arrays (FPGAs) can be programmed to carry out one or more of the systems and procedures described herein. Certain terms are used throughout the following description and Claims to refer to particular system components. As one skilled in the art will appreciate, components may be referred to by different names. This document does not intend to distinguish between components that differ in name, but not function.

FIG. 12 is a block diagram illustrating an example computing device 1250. Computing device 1250 may be used to perform various procedures, such as those discussed herein. Computing device 1250 can function as a server, a client, or any other computing entity. Computing device 1250 can perform various monitoring functions as discussed herein, and can execute one or more application programs, such as the application programs described herein. Computing device 1250 can be any of a wide variety of computing devices, such as a desktop computer, a notebook computer, a server computer, a handheld computer, camera control unit, tablet computer and the like.

Computing device 1250 includes one or more processor(s) 1252, one or more memory device(s) 1254, one or more interface(s) 1256, one or more mass storage device(s) 1258, one or more Input/Output (I/O) device(s) 1260, and a display device 1280 all of which are coupled to a bus 1262. Processor(s) 1252 include one or more processors or controllers that execute instructions stored in memory device(s) 1254 and/or mass storage device(s) 1258. Processor(s) 1252 may also include various types of computer-readable media, such as cache memory.

Memory device(s) 1254 include various computer-readable media, such as volatile memory (e.g., random access memory (RAM) 1264) and/or nonvolatile memory (e.g., read-only memory (ROM) 1266). Memory device(s) 1254 may also include rewritable ROM, such as Flash memory.

Mass storage device(s) 1258 include various computer readable media, such as magnetic tapes, magnetic disks, optical disks, solid-state memory (e.g., Flash memory), and so forth. As shown in FIG. 2, a particular mass storage device is a hard disk drive 1274. Various drives may also be included in mass storage device(s) 1258 to enable reading from and/or writing to the various computer readable media. Mass storage device(s) 1258 include removable media 1276 and/or non-removable media.

I/O device(s) 1260 include various devices that allow data and/or other information to be input to or retrieved from computing device 1250. Example I/O device(s) 1260 include digital imaging devices, electromagnetic sensors and emitters, cursor control devices, keyboards, keypads, microphones, monitors or other display devices, speakers, printers, network interface cards, modems, lenses, CCDs or other image capture devices, and the like.

Display device 1280 includes any type of device capable of displaying information to one or more users of computing device 1250. Examples of display device 1280 include a monitor, display terminal, video projection device, and the like.

Interface(s) 1206 include various interfaces that allow computing device 1250 to interact with other systems, devices, or computing environments. Example interface(s) 1256 may include any number of different network interfaces 1270, such as interfaces to local area networks (LANs), wide area networks (WANs), wireless networks, and the Internet. Other interface(s) include user interface 1268 and peripheral device interface 1272. The interface(s) 1256 may also include one or more user interface elements 1268. The interface(s) 1256 may also include one or more peripheral interfaces such as interfaces for printers, pointing devices (mice, track pad, etc.), keyboards, and the like.

Bus 1262 allows processor(s) 1252, memory device(s) 1254, interface(s) 1256, mass storage device(s) 1258, and I/O device(s) 1260 to communicate with one another, as well as other devices or components coupled to bus 1262. Bus 1262 represents one or more of several types of bus structures, such as a system bus, PCI bus, IEEE 1394 bus, USB bus, and so forth.

For purposes of illustration, programs and other executable program components are shown herein as discrete blocks, although it is understood that such programs and components may reside at various times in different storage components of computing device 1250 and are executed by processor(s) 1252. Alternatively, the systems and procedures described herein can be implemented in hardware, or a combination of hardware, software, and/or firmware. For example, one or more application specific integrated circuits (ASICs) or field programmable gate arrays (FPGAs) can be programmed to carry out one or more of the systems and procedures described herein.

Figure 12A:
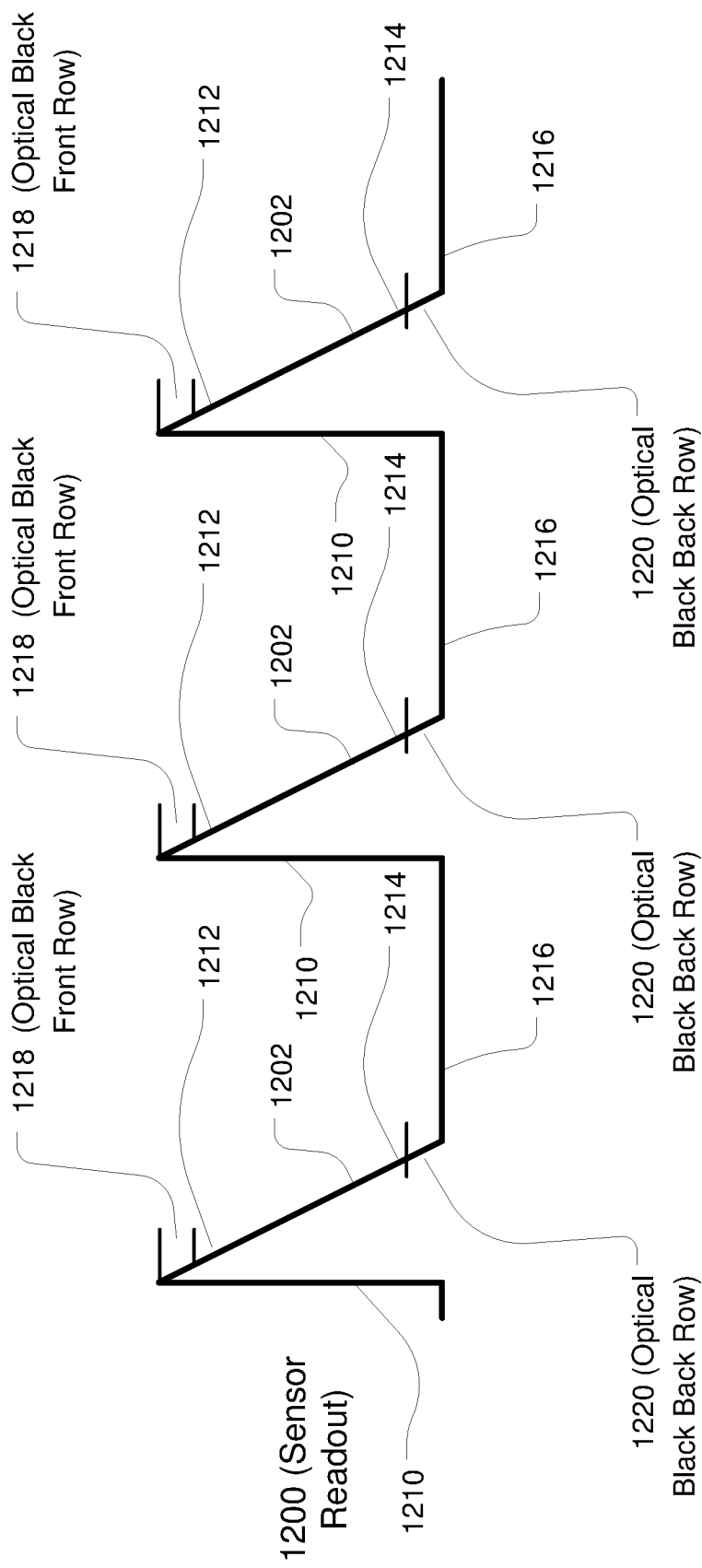
Figure 12D:
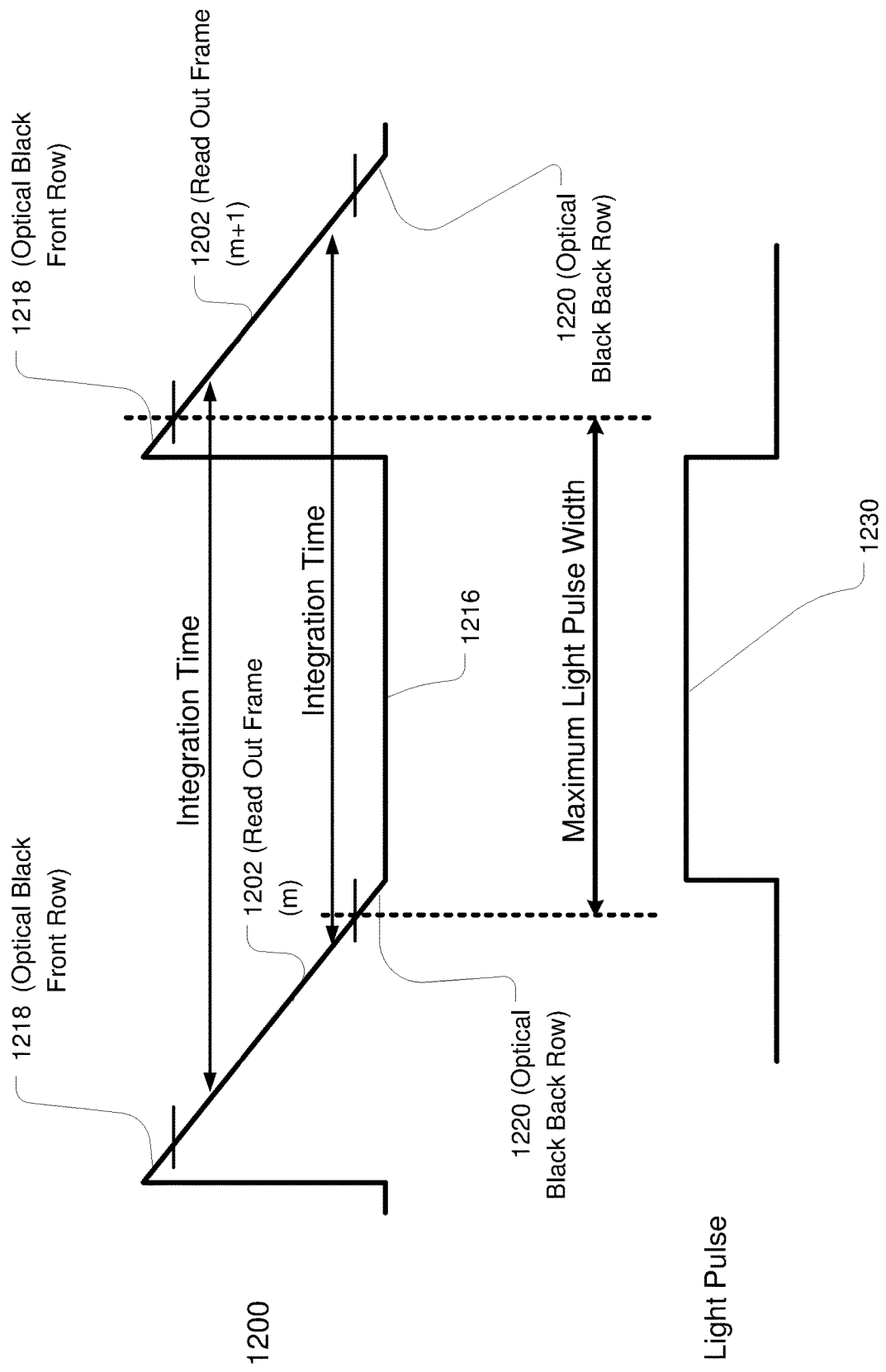

FIG. 12A illustrates the operational cycles of a sensor used in rolling readout mode or during the sensor readout 1200. The frame readout may start at and may be represented by vertical line 1210. The read out period is represented by the diagonal or slanted line 1202. The sensor may be read out on a row by row basis, the top of the downwards slanted edge being the sensor top row 1212 and the bottom of the downwards slanted edge being the sensor bottom row 1214. The time between the last row readout and the next readout cycle may be called the blanking time 1216. It should be noted that some of the sensor pixel rows might be covered with a light shield (e.g., a metal coating or any other substantially black layer of another material type). These covered pixel rows may be referred to as optical black rows 1218 and 1220. Optical black rows 1218 and 1220 may be used as input for correction algorithms. As shown in FIG. 12A, these optical black rows 1218 and 1220 may be located on the top of the pixel array or at the bottom of the pixel array or at the top and the bottom of the pixel array. FIG. 12B illustrates a process of controlling the amount of electromagnetic radiation, e.g., light, that is exposed to a pixel, thereby integrated or accumulated by the pixel. It will be appreciated that photons are elementary particles of electromagnetic radiation. Photons are integrated, absorbed, or accumulated by each pixel and converted into an electrical charge or current. An electronic shutter or rolling shutter (shown by dashed line 1222) may be used to start the integration time by resetting the pixel. The light will then integrate until the next readout phase. The position of the electronic shutter 1222 can be moved between two readout cycles 1202 in order to control the pixel saturation for a given amount of light. It should be noted that this technique allows for a constant integration time between two different lines, but introduces a delay when moving from top to bottom rows. FIG. 12C illustrates the case where the electronic shutter 1222 has been removed. In this configuration, the integration of the incoming light may start during readout 1202 and may end at the next readout cycle 1202, which also defines the start of the next integration. FIG. 12D shows a configuration without an electronic shutter 1222, but with a controlled and pulsed light 1230 during the blanking time 1216. This ensures that all rows see the same light issued from the same light pulse 1230. In other words, each row will start its integration in a dark environment, which may be at the optical black back row 1220 of read out frame (m) for a maximum light pulse width and will then receive a light strobe and will end its integration in a dark environment, which may be at the optical black front row 1218 of the next succeeding read out frame (m+1) for a maximum light pulse width. In FIG. 12D for example, the image generated from the light pulse will be solely available during frame (m+1) readout without any interference with frames (m) and (m+2). It should be noted that the condition to have a light pulse to be read out only in one frame and not interfere with neighboring frames is to have the given light pulse firing during the blanking time 1216. Because the optical black rows 1218, 1220 are insensitive to light, the optical black back rows 1220 time of frame (m) and the optical black front rows 1218 time of frame (m+1) can be added to the blanking time 1216 to determine the maximum range of the firing time of the light pulse 1230. As illustrated in FIG. 12A, a sensor may be cycled many times in order to receive data for each pulsed color (e.g., Red, Green, Blue). Each cycle may be timed. In an embodiment, the cycles may be timed to operate within an interval of 16.67 ms. In another embodiment, the cycles may be timed to operate within an interval of 8.3 ms. It will be appreciated that other timing intervals are contemplated by the disclosure and are intended to fall within the scope of this disclosure.

Figure 13:
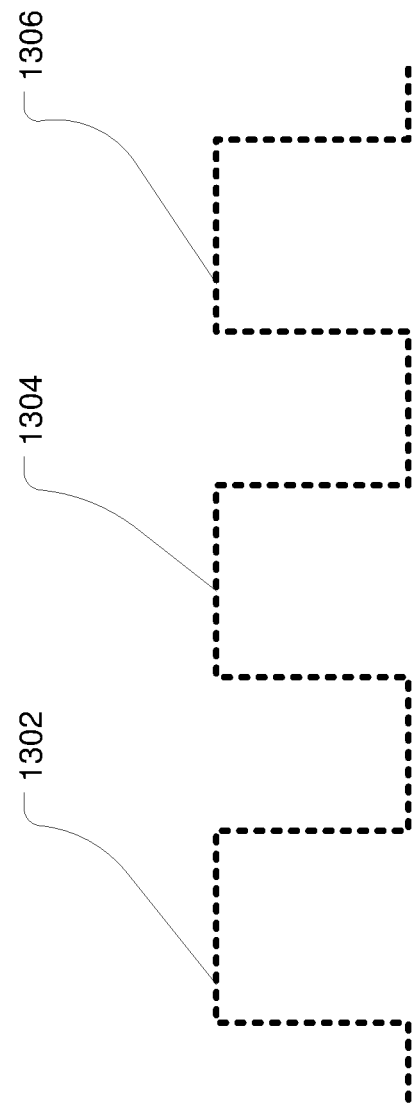
FIG. 13 illustrates a graphical representation of the operation of an embodiment of an electromagnetic emitter.

FIG. 13 graphically illustrates the operation of an embodiment of an electromagnetic emitter. An emitter may be timed to correspond with the cycles of a sensor, such that electromagnetic radiation is emitted within the sensor operation cycle and/or during a portion of the sensor operation cycle. FIG. 13 illustrates Pulse 1 at 1302, Pulse 2 at 1304, and Pulse 3 at 1306. In an embodiment, the emitter may pulse during the read out portion 1202 of the sensor operation cycle. In an embodiment, the emitter may pulse during the blanking portion 1216 of the sensor operation cycle. In an embodiment, the emitter may pulse for a duration that is during portions of two or more sensor operational cycles. In an embodiment, the emitter may begin a pulse during the blanking portion 1216, or during the optical black portion 1220 of the readout portion 1202, and end the pulse during the readout portion 1202, or during the optical black portion 1218 of the readout portion 1202 of the next succeeding cycle. It will be understood that any combination of the above is intended to fall within the scope of this disclosure as long as the pulse of the emitter and the cycle of the sensor correspond.

Figure 14:
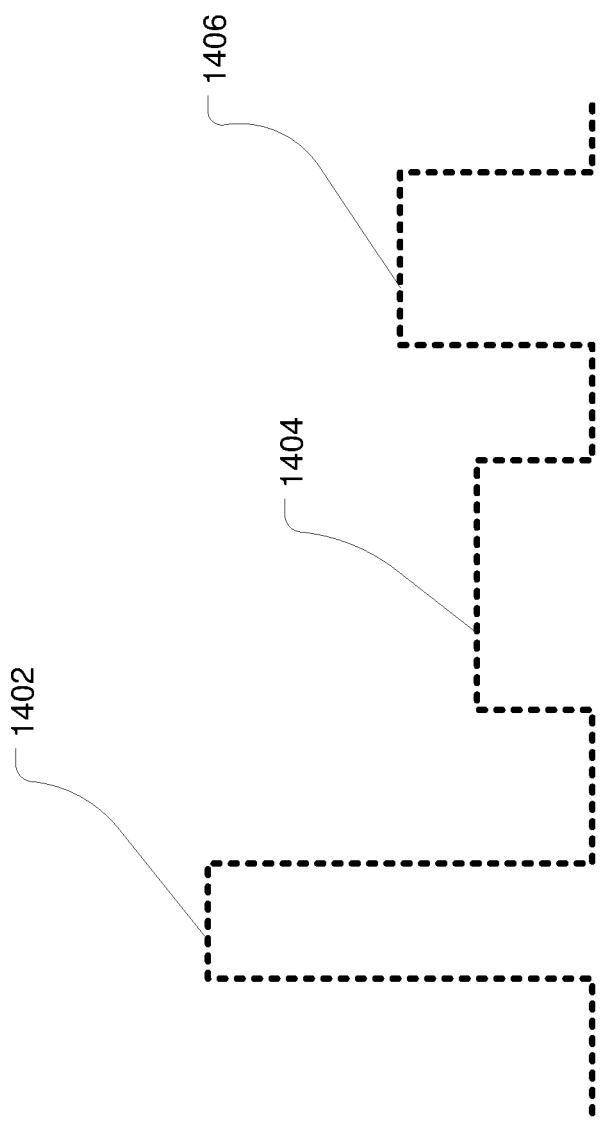
FIG. 14 illustrates a graphical representation of varying the duration and magnitude of the emitted electromagnetic pulse in order to provide exposure control.

FIG. 14 graphically represents varying the duration and magnitude of the emitted electromagnetic pulse (e.g., Pulse 1 at 1402, Pulse 2 at 1404, and Pulse 3 at 1406) to control exposure. An emitter having a fixed output magnitude may be pulsed during any of the cycles noted above in relation to FIGS. 12D and 13 for an interval to provide the needed electromagnetic energy to the pixel array. An emitter having a fixed output magnitude may be pulsed at a longer interval of time, thereby providing more electromagnetic energy to the pixels or the emitter may be pulsed at a shorter interval of time, thereby providing less electromagnetic energy. Whether a longer or shorter interval time is needed depends upon the operational conditions.

In contrast to adjusting the interval of time that the emitter pulses a fixed output magnitude, the magnitude of the emission itself may be increased in order to provide more electromagnetic energy to the pixels. Similarly, decreasing the magnitude of the pulse provides less electromagnetic energy to the pixels. It should be noted that an embodiment of the system may have the ability to adjust both magnitude and duration concurrently, if desired. Additionally, the sensor may be adjusted to increase its sensitivity and duration as desired for optimal image quality. FIG. 14 illustrates varying the magnitude and duration of the pulses. In the illustration, Pulse 1 at 1402 has a higher magnitude or intensity than either Pulse 2 at 1404 or Pulse 3 at 1406. Additionally, Pulse 1 at 1402 has a shorter duration than Pulse 2 at 1404 or Pulse 3 at 1406, such that the electromagnetic energy provided by the pulse is illustrated by the area under the pulse shown in the illustration. In the illustration, Pulse 2 at 1404 has a relatively low magnitude or intensity and a longer duration when compared to either Pulse 1 at 1402 or Pulse 3 at 1406. Finally, in the illustration, Pulse 3 at 1406 has an intermediate magnitude or intensity and duration, when compared to Pulse 1 at 1402 and Pulse 2 at 1404.

Figure 15:
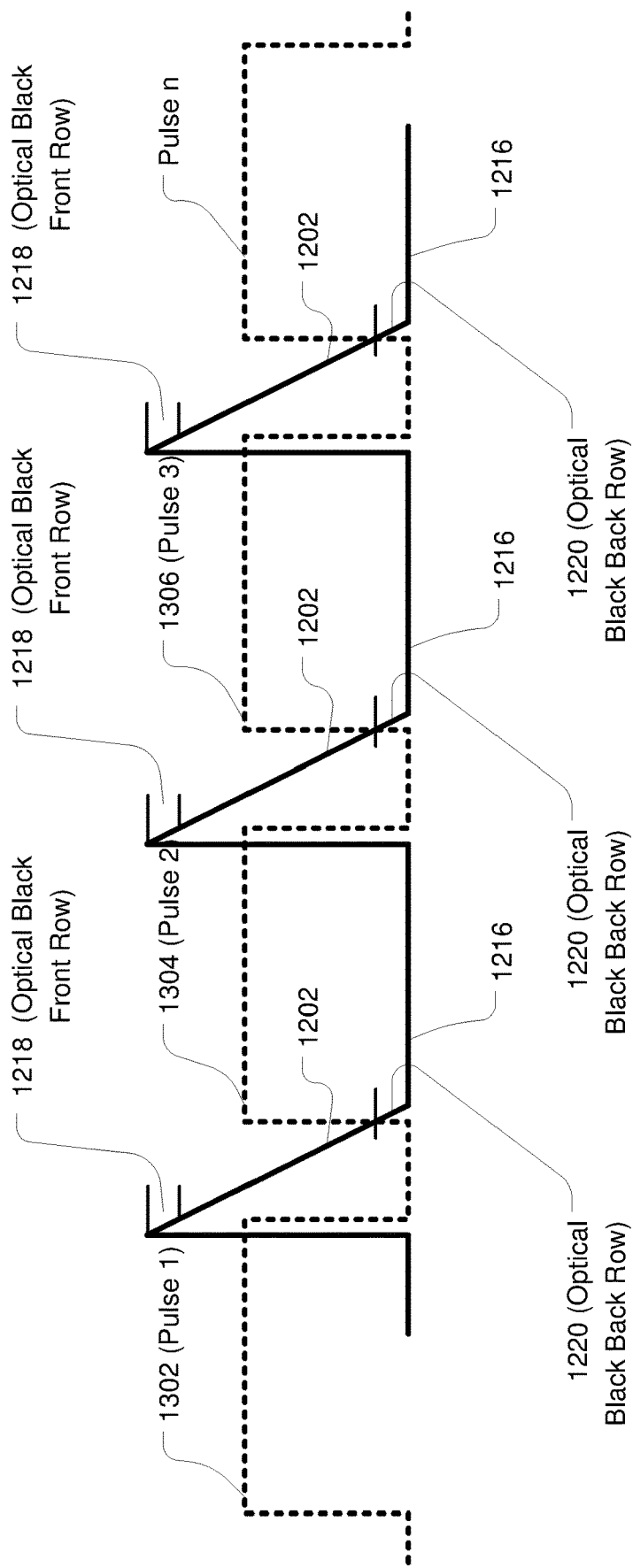
FIG. 15 illustrates a graphical representation of an embodiment of the disclosure combining the operational cycles of a sensor, the electromagnetic emitter and the emitted electromagnetic pulses of FIGS. 12A-14, which demonstrate the imaging system during operation.

FIG. 15 is a graphical representation of an embodiment of the disclosure combining the operational cycles, the electromagnetic emitter and the emitted electromagnetic pulses of FIGS. 12A-14 to demonstrate the imaging system during operation in accordance with the principles and teachings of the disclosure. As can be seen in the figure, the electromagnetic emitter pulses the emissions primarily during the blanking period 1216 of the sensor, such that the pixels will be charged and ready to read during the read out portion 1202 of the sensor cycle. The dashed line portions in the pulse (from FIG. 13) illustrate the potential or ability to emit electromagnetic energy during the optical black portions 1220 and 1218 of the read cycle (sensor cycle) 1200 if additional time is needed or desired to pulse electromagnetic energy.

Figure 16:
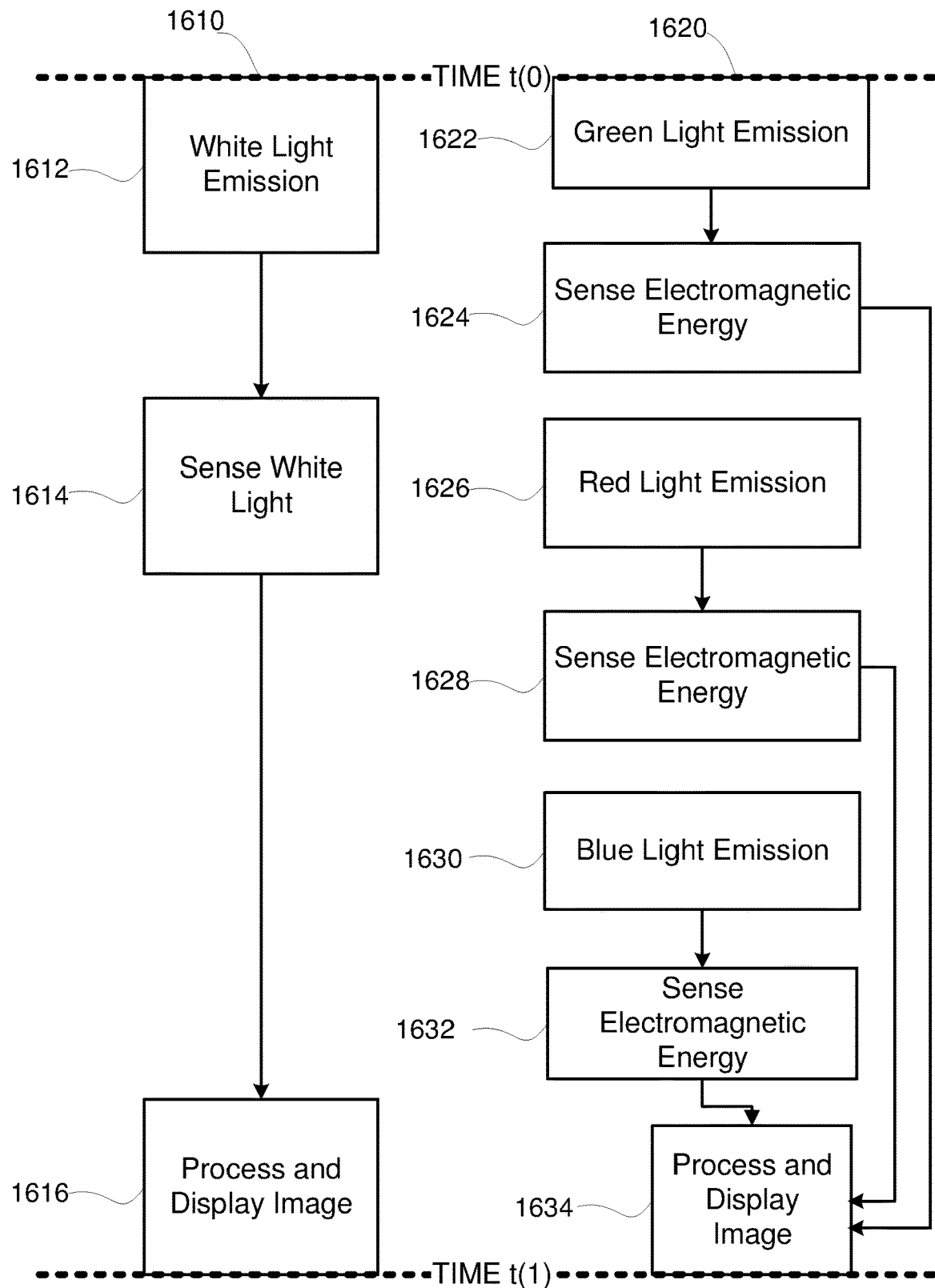
FIG. 16 illustrates a schematic of two distinct processes over a period of time from t(0) to t(1) for recording a frame of video for full spectrum light and partitioned spectrum light.

FIG. 16 illustrates a schematic of two distinct processes over a period of time from t(0) to t(1) for recording a frame of video for full spectrum light and partitioned spectrum light. It should be noted that color sensors have a color filter array (CFA) for filtering out certain wavelengths of light per pixel commonly used for full spectrum light reception. An example of a CFA is a Bayer pattern. Because the color sensor may comprise pixels within the array that are made sensitive to a single color from within the full spectrum, a reduced resolution image results because the pixel array has pixel spaces dedicated to only a single color of light within the full spectrum. Usually such an arrangement is formed in a checkerboard type pattern across the entire array.

In contrast, when partitioned spectrums of light are used a sensor can be made to be sensitive or responsive to the magnitude of all light energy because the pixel array will be instructed that it is sensing electromagnetic energy from a predetermined partition of the full spectrum of electromagnetic energy in each cycle. Therefore, to form an image the sensor need only be cycled with a plurality of differing partitions from within the full spectrum of light and then reassembling the image to display a predetermined mixture of color values for every pixel across the array. Accordingly, a higher resolution image is also provided because there are reduced distances as compared to a Bayer sensor between pixel centers of the same color sensitivity for each of the color pulses. As a result, the formed colored image has a higher modulation transfer function (MTF). Because the image from each color partition frame cycle, has a higher resolution, the resultant image created when the partitioned light frames are combined into a full color frame, also has a higher resolution. In other words, because each and every pixel within the array (instead of, at most, every second pixel in a sensor with color filter) is sensing the magnitudes of energy for a given pulse and a given scene, just fractions of time apart, a higher resolution image is created for each scene with less derived (less accurate) data needing to be introduced.

For example, white or full spectrum visible light is a combination of red, green and blue light. In the embodiment shown in FIG. 16, it can be seen that in both the partitioned spectrum process 1620 and full spectrum process 1610 the time to capture an image is t(0) to t(1). In the full spectrum process 1610, white light or full spectrum electromagnetic energy is emitted at 1612. At 1614, the white or full spectrum electromagnetic energy is sensed. At 1616, the image is processed and displayed. Thus, between time t(0) and t(1), the image has been processed and displayed. Conversely, in the partitioned spectrum process 1620, a first partition is emitted at 1622 and sensed at 1624. At 1626, a second partition is emitted and then sensed at 1628. At 1630, a third partition is emitted and sensed at 1632. At 1634, the image is processed and displayed. It will be appreciated that any system using an image sensor cycle that is at least two times faster than the white light cycle is intended to fall within the scope of the disclosure.

As can be seen graphically in the embodiment illustrated in FIG. 16 between times t(0) and t(1), the sensor for the partitioned spectrum system 1620 has cycled three times for every one of the full spectrum system. In the partitioned spectrum system 1620, the first of the three sensor cycles is for a green spectrum 1622 and 1624, the second of the three is for a red spectrum 1626 and 1628, and the third is for a blue spectrum 1630 and 1632. Thus, in an embodiment, wherein the display device (LCD panel) operates at 50-60 frames per second, a partitioned light system should operate at 150-180 frames per second to maintain the continuity and smoothness of the displayed video.

In other embodiments there may be different capture and display frame rates. Furthermore, the average capture rate could be any multiple of the display rate.

In an embodiment it may be desired that not all partitions be represented equally within the system frame rate. In other words, not all light sources have to be pulsed with the same regularity so as to emphasize and de-emphasize aspects of the recorded scene as desired by the users. It should also be understood that non-visible and visible partitions of the electromagnetic spectrum may be pulsed together within a system with their respective data value being stitched into the video output as desired for display to a user.

An embodiment may comprise a pulse cycle pattern as follows:
 Green pulse;
 Red pulse;
 Blue pulse;
 Green pulse;
 Red pulse;
 Blue pulse;
 Infra-red (IR) pulse;
 (Repeat)

As can be seen in the example, an IR partition may be pulsed at a rate differing from the rates of the other partition pulses. This may be done to emphasize a certain aspect of the scene, with the IR data simply being overlaid with the other data in the video output to make the desired emphasis. It should be noted that the addition of a fourth electromagnetic partition does not necessarily require the serialized system to operate at four times the rate of a full spectrum non-serial system because every partition does not have to be represented equally in the pulse pattern. As seen in the embodiment, the addition of a partition pulse that is represented less in a pulse pattern (IR in the above example), would result in an increase of less than 20% of the cycling speed of the sensor in order accommodate the irregular partition sampling.

In an embodiment, an electromagnetic partition may be emitted that is sensitive to dyes or materials that are used to highlight aspects of a scene. In the embodiment it may be sufficient to highlight the location of the dyes or materials without need for high resolution. In such an embodiment, the dye sensitive electromagnetic partition may be cycled much less frequently than the other partitions in the system in order to include the emphasized data. The partition cycles may be divided so as to accommodate or approximate various imaging and video standards.

It will be appreciated that various features disclosed herein provide significant advantages and advancements in the art. The following claims are exemplary of some of those features.

EXAMPLES

The following examples pertain to features of further embodiments of the disclosure:

Example 1. A system comprising:
a scope including a lens;
a hand piece;
an imaging sensor, the imaging sensor including a two thousand pixel by two thousand pixel array of pixels;
interface elements which, when actuated, cause an angle of view provided through the lens to be changed in a single image readout frame.

Example 2. An exemplary embodiment includes example 1, wherein the lens is a 125°-180° lens.

Example 3. An exemplary embodiment includes any of examples 1 and 2, wherein the angle of view may be changed to a 30° angle of view.

Example 4. An exemplary embodiment includes any of examples 1-3, wherein the angle of view may be changed to a 70° angle of view.

Example 5. An exemplary embodiment includes any of examples 1-4, further comprising image acquisition and processing circuitry which identifies a one thousand pixel by one thousand pixel array of pixels in the two thousand pixel by two thousand pixel array of pixels that corresponds to pixels that are exposed to image information for the angle of view.

Example 6. An exemplary embodiment includes any of examples 1-5, wherein when the angle of view provided through the lens is changed to a second angle of view, the image acquisition and processing circuitry identifies a second one thousand pixel by one thousand pixel array of pixels in the two thousand pixel by two thousand pixel array of pixels that corresponds to pixels that are exposed to image information for the second angle of view.

Example 7. An exemplary embodiment includes any of examples 1-6, wherein the angle of view is digitally rotatable in response to activation of one of the interface elements.

Example 8. An exemplary embodiment includes any of examples 1-7, further comprising image acquisition and processing circuitry which identifies a one thousand pixel by one thousand pixel array of pixels in the two thousand pixel by two thousand pixel array of pixels that corresponds to the pixels that are exposed to image information for the angle of view at a first position.

Example 9. An exemplary embodiment includes any of examples 1-8, wherein the image acquisition and processing circuitry detects that the angle of view has been rotated to a second position and, in response, identifies a second one thousand pixel by one thousand pixel array of pixels in the two thousand pixel by two thousand pixel array of pixels that corresponds to the pixels that are exposed to image information for the angle of view at the second position.

Example 10. An exemplary embodiment includes any of examples 1-9, further comprising a notch which is displayed on a display device along with information retrieved from the imaging sensor.

Example 11. A scope, comprising:
a lens disposed in a distal tip of the scope;
a hand piece;
an imaging sensor, the imaging sensor including a two thousand pixel by two thousand pixel array of pixels;
interface elements which, when actuated, cause an angle of view provided through the lens to be changed in a single image readout frame.

Example 12. An exemplary embodiment includes example 11, wherein the lens is a 125°-180° lens.

Example 13. An exemplary embodiment includes any of examples 11 and 12, wherein the angle of view is 0°.

Example 14. An exemplary embodiment includes any of examples 11-13, wherein the angle of view is 30°.

Example 15. An exemplary embodiment includes any of examples 11-14, wherein the angle of view is 70°.

Example 16. An exemplary embodiment includes any of examples 11-15, wherein the imaging sensor identifies a first one thousand pixel by one thousand pixel array of pixels within the two thousand pixel by two thousand pixel array of pixels which contains image information for a 0° angle of view.

Example 17. An exemplary embodiment includes any of examples 11-16, further comprising image acquisition and processing circuitry which detects a rotation of the angle of view and, in response, identifies a second one thousand pixel by one thousand pixel array of pixels within the two thousand pixel by two thousand pixel array which contains image data representative of a rotated 0° angle of view.

Example 18. An exemplary embodiment includes any of examples 11-17, wherein the imaging sensor identifies a first one thousand pixel by one thousand pixel array of pixels within the two thousand by two thousand pixel array of pixels which contains image information for a 30° angle of view.

Example 19. An exemplary embodiment includes any of examples 11-18, further comprising image acquisition and processing circuitry which detects a rotation of the angle of view and, in response, identifies a second one thousand pixel by one thousand pixel array of pixels within the two thousand pixel by two thousand pixel array which contains image data representative of a rotated 30° angle of view.

Example 20. An exemplary embodiment includes any of examples 11-19, wherein the imaging sensor identifies a first one thousand pixel by one thousand pixel array of pixels within the two thousand by two thousand pixel array of pixels which contains image information for a 70° angle of view.

Example 21. An exemplary embodiment includes any of examples 11-20, further comprising image acquisition and processing circuitry which detects a rotation of the angle of view and, in response, identifies a second one thousand pixel by one thousand pixel array of pixels within the two thousand pixel by two thousand pixel array which contains image data representative of a rotated 70° angle of view.

Example 22. A method, comprising
providing a scope having a lens in a distal tip of the scope and having one or more interface elements;
receiving an indication, from one of the one or more interface elements, to change an angle of view provided to a display device;
identifying, by a processor, a one thousand pixel by one thousand pixel set of pixels on an image sensor having a two thousand pixel by two thousand pixel array of pixels corresponding to the indicated angle of view;
receiving, by a processor, imaging data from the one thousand pixel by one thousand pixel set of pixels corresponding to the indicated angle of view; and
generating an image from the image data for display on the display device with the changed angle of view.

Example 23. An exemplary embodiment includes example 22, further comprising exposing the one thousand pixel by one thousand pixel set corresponding to the indicated angle of view.

Example 24. An exemplary embodiment includes any of examples 22 and 23, wherein the two thousand pixel by two thousand pixel array of pixels provides a 4K imaging sensor.

Example 25. An exemplary embodiment includes any of examples 22-24, wherein the angle of view is changed from 0° to 30°.

Example 26. An exemplary embodiment includes any of examples 22-25, wherein the angle of view is changed from 0° to 70°.

Example 27. An exemplary embodiment includes any of examples 22-26, wherein the angle of view is changed from 30° to 70°.

Example 28. An exemplary embodiment includes any of examples 22-27, wherein the angle of view is changed from 30° to 0°.

Example 29. An exemplary embodiment includes any of examples 22-28, wherein the angle of view is changed from 70° to 0°.

Example 30. An exemplary embodiment includes any of examples 22-29, wherein the angle of view is changed from 70° to 30°.

Example 31. An exemplary embodiment includes any of examples 22-30, further comprising: receiving, by a processor and from one of the one or more interface elements, an indication of a degree of rotation of the angle of view and a second rotated angle of view corresponding to the indicated degree of rotation for the angle of view and, in response, identifying, by a processor, a second one thousand pixel by one thousand pixel array of pixels corresponding to the second rotated angle of view.

It is to be understood that any features of the above-described arrangements, examples and embodiments may be combined in a single embodiment comprising any combination of features taken from any of the disclosed arrangements, examples and embodiments.

In the foregoing Detailed Description of the Disclosure, various features of the disclosure are grouped together in a single embodiment for the purpose of streamlining the disclosure. This method of disclosure is not to be interpreted as reflecting an intention that the claimed disclosure requires more features than are expressly recited in each claim. Rather, inventive aspects lie in less than all features of a single foregoing disclosed embodiment.

It is to be understood that the above-described arrangements are only illustrative of the application of the principles of the disclosure. Numerous modifications and alternative arrangements may be devised by those skilled in the art without departing from the spirit and scope of the disclosure and the appended claims are intended to cover such modifications and arrangements.

Thus, while the disclosure has been shown in the drawings and described above with particularity and detail, it will be apparent to those of ordinary skill in the art that numerous modifications, including, but not limited to, variations in size, materials, shape, form, function and manner of operation, assembly and use may be made without departing from the principles and concepts set forth herein.

Further, where appropriate, functions described herein can be performed in one or more of: hardware, software, firmware, digital components, or analog components. For example, one or more application specific integrated circuits (ASICs) or field programmable gate arrays (FPGAs) can be programmed to carry out one or more of the systems and procedures described herein. Certain terms are used throughout the following description and claims to refer to particular system components. As one skilled in the art will appreciate, components may be referred to by different names. This document does not intend to distinguish between components that differ in name, but not function.

The foregoing description has been presented for the purposes of illustration and description. It is not intended to be exhaustive or to limit the disclosure to the precise form disclosed. Many modifications and variations are possible in light of the above teaching. Further, it should be noted that any or all of the aforementioned alternate implementations may be used in any combination desired to form additional hybrid implementations of the disclosure.

Further, although specific implementations of the disclosure have been described and illustrated, the disclosure is not to be limited to the specific forms or arrangements of parts so described and illustrated. The scope of the disclosure is to be defined by the claims appended hereto, any future claims submitted here and in different applications and their equivalents.

What is claimed is:

1. A system comprising:
a single image sensor comprising a pixel array, wherein the pixel array of the single image sensor comprises a plurality of subarrays that each comprises fewer pixels than all pixels in the pixel array;
an interface element for selecting a view pattern for visualizing a scene; and
a processor in communication with the single image sensor and the interface element;
wherein, for at least one readout period of the single image sensor, the processor instructs the single image sensor to read out only one subarray of the plurality of subarrays of the pixel array of the single image sensor, such that the single image sensor reads out fewer than all pixels within the pixel array for the at least one readout period of the single image sensor; and
wherein the one subarray of the plurality of subarrays is selected based on input received from the interface element.

2. The system of claim 1, further comprising a lens for providing a field of view for visualizing the scene with the single image sensor.

3. The system of claim 2, further comprising:
a handpiece unit, wherein the interface element is disposed on the handpiece unit;
a tube; and
wherein the lens is disposed at a distal end of the tube.

4. The system of claim 2, wherein the field of view provided by the lens is digitally partitioned into a plurality of view patterns by selectively reading out the plurality of subarrays of the single image sensor.

5. The system of claim 2, wherein the field of view provided by the lens is within a range from 125° to 180°.

6. The system of claim 2, wherein the lens is a wide-angle lens.

7. The system of claim 2, wherein the lens provides a 0° offset, and wherein the single image sensor digitally approximates the selected view pattern by reading out only the one subarray of the plurality of subarrays of the pixel array.

8. The system of claim 1, wherein the single image sensor reads out only the pixels within the one subarray of the single image sensor to digitally implement the selected view pattern.

9. The system of claim 1, wherein the single image sensor reads out only the one subarray of the plurality of subarrays of the pixel array to digitally implement the selected view pattern based on the input from the interface element.

10. The system of claim 1, wherein the single image sensor is a 4K image sensor, and wherein the selected view pattern approximates an angle of view selected by a user, and wherein the single image sensor senses the selected view pattern by reading out only a one-thousand-pixel by one-thousand-pixel subarray of the 4K image sensor.

11. The system of claim 1, wherein the selected view pattern approximates a 30° offset such that the single image sensor approximates visualizing a scene through a 30° prism by reading out only the one subarray of the plurality of subarrays of the pixel array.

12. The system of claim 1, wherein the selected view pattern approximates a 70° offset such that the single image sensor approximates visualizing a scene through a 70° prism by reading out only the one subarray of the plurality of subarrays of the pixel array.

13. The system of claim 1, further comprising an emitter for pulsing a plurality of pulses of electromagnetic radiation, wherein the plurality of pulses of electromagnetic radiation comprises a visible wavelength of electromagnetic radiation and a non-visible wavelength of electromagnetic radiation.

14. The system of claim 13, wherein the emitter pulses electromagnetic radiation during a blanking period of the single image sensor, and wherein the emitter cycles off during a readout period of the single image sensor.

15. The system of claim 13, wherein the processor synchronizes timing of the single image sensor and the emitter such that the emitter pulses electromagnetic radiation during a blanking period of the single image sensor, and wherein the emitter pulses a pulse cycle pattern comprising one or more of: a visible wavelength, a near-infrared wavelength, an infrared wavelength, an ultraviolet wavelength, or a multispectral wavelength.

16. The system of claim 13, wherein the plurality of pulses of electromagnetic radiation comprises an ultraviolet emission.

17. The system of claim 1, wherein the input received from the interface element comprises a selection of the view pattern, and wherein a user may actuate the interface element to change the view pattern during operation.

18. The system of claim 1, wherein the view pattern approximates an offset angle of view provided by a prism for visualizing the scene, and wherein the view pattern comprises one or more of a 30° angle of view, a 0° angle of view, or a 70° angle of view.

19. The system of claim 1, wherein the processor instructs the single image sensor to read out two subarrays of the plurality of subarrays for sensing two image frames in a single readout period, wherein the two image frames comprise:
- a first image frame comprising a first view pattern, wherein the first view pattern represents a first portion of a field of view provided by a lens; and
- a second image frame comprising a second view pattern, wherein the second view pattern represents a second portion of the field of view provided by the lens.

20. The system of claim 19, wherein the first view pattern is different from the second view pattern, and wherein the first view pattern is sensed by a first subarray of the pixel array and the second view pattern is sensed by a second subarray of the pixel array during the single readout period.

* * * * *